(12) United States Patent
Cheikh

(10) Patent No.: US 6,306,420 B1
(45) Date of Patent: Oct. 23, 2001

(54) METHODS AND APPARATUS FOR THE DELIVERY OF SOLID DRUG COMPOSITIONS

(75) Inventor: Roland Cherif Cheikh, Issy-les-Moulineaux (FR)

(73) Assignee: Societe de Conseils de Recherches et d'Applications Scientifiques, S.A.S., Paris (FR)

(*) Notice: Subject to any disclaimer, the term of this patent is extended or adjusted under 35 U.S.C. 154(b) by 0 days.

(21) Appl. No.: 09/574,419

(22) Filed: May 19, 2000

Related U.S. Application Data

(62) Division of application No. 09/110,880, filed on Jul. 7, 1998, which is a division of application No. 08/459,514, filed on Jun. 2, 1995, now Pat. No. 5,660,846, which is a continuation of application No. 08/300,138, filed on Sep. 2, 1994, now Pat. No. 5,837,276.

(51) Int. Cl.⁷ .............. A61F 13/00; A61F 2/00; A61K 9/22
(52) U.S. Cl. .......................... 424/422; 424/423
(58) Field of Search .................. 424/422, 423; 604/891.1

(56) References Cited

U.S. PATENT DOCUMENTS

| | | |
|---|---|---|
| 2,513,014 | 6/1950 | Fields . |
| 3,692,027 | 9/1972 | Ellinwood, Jr. .............. 128/260 |
| 3,760,806 | 9/1973 | Leeper ........................ 128/260 |
| 3,995,631 | 12/1976 | Higuchi et al. ................ 128/260 |

(List continued on next page.)

FOREIGN PATENT DOCUMENTS

| | | |
|---|---|---|
| 33 17 536 | 11/1984 | (DE) . |
| 3317536 | 11/1984 | (DE) . |
| 0049 068 | 4/1982 | (EP) . |
| 0 134 318 | 3/1985 | (EP) . |
| 0 139 286 A2 | 5/1985 | (EP) . |
| 0 230 647 | 8/1987 | (EP) . |
| 0 292 936 A2 | 11/1988 | (EP) . |
| 0 403 032 | 12/1990 | (EP) . |
| 2 239 989 | 3/1975 | (FR) . |
| WO 93/2301 | 11/1993 | (WO) . |
| WO 94/22423 | 10/1994 | (WO) . |
| WO 9522314 | 8/1995 | (WO) . |

OTHER PUBLICATIONS

Database WPI; Section Ch, Week 199242;Derwent Publication Ltd., London, GB; AN 1992–124827; XP–002126337 & JP 04 244031 A (ZH Kankoku Kagaku Gijutsu Kenk), Sep. 1, 1992; Abstract.

Primary Examiner—Thurman K. Page
Assistant Examiner—Todd D Ware
(74) Attorney, Agent, or Firm—Brian R. Morrill; Fish & Richardson; Alan F. Feeney

(57) ABSTRACT

The invention features an implantable device for the automatic delivery of an active ingredient according to an adjustable delivery profile. The device includes a housing; a reservoir operatively connected to the housing and arranged to store a solid composition including the active ingredient; an actuator arranged within the housing to move the solid composition from the reservoir to a transit area, wherein the solid composition exits the housing at the transit area; a controller that acts on the actuator to adjust movement of the solid composition out of the housing according to the adjustable delivery profile; and a power source arranged to provide energy to the actuator and the controller. The solid composition can be an elongate, solid composition comprising a drug, and up to 90% of a carrier, wherein the composition has a cross-section of less than 0.5 mm, and wherein the drug and the carrier are selected and compounded in a proportion such that the drug is immediately released from the carrier upon contact with a liquid.

7 Claims, 16 Drawing Sheets

U.S. PATENT DOCUMENTS

| | | | |
|---|---|---|---|
| 3,995,632 | 12/1976 | Nakano et al. | 128/260 |
| 4,086,914 | 5/1978 | Moore | 128/1.2 |
| 4,093,708 | 6/1978 | Zaffaroni et al. | 424/15 |
| 4,177,256 | 12/1979 | Michaels et al. | 424/22 |
| 4,263,910 | 4/1981 | Pardekooper et al. | 128/217 |
| 4,315,516 | 2/1982 | Zappell | 132/90 |
| 4,327,725 | 5/1982 | Cortese et al. | 128/260 |
| 4,340,054 | 7/1982 | Michaels | 128/260 |
| 4,344,743 | 8/1982 | Bessman et al. | 417/317 |
| 4,360,019 | 11/1982 | Portner et al. | 128/213 R |
| 4,451,253 | 5/1984 | Harman | 604/60 |
| 4,581,018 | 4/1986 | Jassawalla et al. | 604/153 |
| 4,595,583 | 6/1986 | Eckenhoff et al. | 424/15 |
| 4,596,575 | 6/1986 | Rosenberg et al. | 604/891 |
| 4,661,103 | 4/1987 | Harman | 604/62 |
| 4,711,251 | 12/1987 | Stokes | 128/784 |
| 4,720,384 | 1/1988 | Di Luccio et al. | 424/78 |
| 4,723,958 | 2/1988 | Pope et al. | 604/890.1 |
| 4,753,636 | 6/1988 | Free | 604/49 |
| 4,772,263 | 9/1988 | Dorman et al. | 604/132 |
| 4,834,704 | 5/1989 | Reinicke | 604/51 |
| 4,886,514 | 12/1989 | Maget | 604/891.1 |
| 4,888,074 | 12/1989 | Pocknell | 156/217 |
| 4,900,304 | 2/1990 | Fujioka et al. | 604/60 |
| 4,936,827 | 6/1990 | Grimm et al. | 604/60 |
| 4,941,874 | 7/1990 | Sandow et al. | 604/60 |
| 4,944,659 | 7/1990 | Labbe et al. | 417/322 |
| 4,976,966 | 12/1990 | Theeuwes et al. | 424/473 |
| 4,994,028 | 2/1991 | Leonard et al. | 604/60 |
| 5,030,216 | 7/1991 | Theeuwes et al. | 604/892.1 |
| 5,049,141 | 9/1991 | Olive | 604/891.1 |
| 5,086,787 | 2/1992 | Grandjean et al. | 128/786 |
| 5,226,895 | 7/1993 | Harris | 604/208 |
| 5,660,846 * | 8/1997 | Cheikh | 424/423 |
| 5,837,276 * | 11/1998 | Cheikh | 424/423 |

* cited by examiner

METHODS AND APPARATUS FOR THE DELIVERY OF SOLID DRUG COMPOSITIONS

CROSS-REFERENCE TO RELATED APPLICATIONS

This application is a divisional application of U.S. Ser. No. 09/110,880, filed on Jul. 7, 1998, which is a Divisional of U.S. application Ser. No. 08/459,514, filed on Jun. 2, 1995, and issued on Aug. 26, 1997 as U.S. Pat. No. 5,660,846, which is a Continuation of U.S. application Ser. No. 08/300,138, filed on Sep. 2, 1994, and issued on Nov. 17, 1998, as U.S. Pat. No. 5,837,276; all of which are incorporated herein by reference in their entirety.

BACKGROUND OF THE INVENTION

This invention relates to the delivery or administration of solid compositions that include an active ingredient such as a drug.

The effective use of drug compositions, either for an immediate bolus delivery or for a continuous, controlled delivery, often requires parenteral administration in order to achieve the desired effect. Traditionally, parenteral administration is achieved by a liquid injection using a syringe, a perfusion, or a pump. However, these methods cause both inconvenience and discomfort for patients, especially those requiring daily treatments for months or even a lifetime, e.g., diabetics who require one or two injections of insulin daily for the rest of their lives.

Furthermore, the parenteral route usually requires an extemporaneous preparation of a liquid drug formulation, which can lead to instability of the drug and waste of the drug in the formulation. In addition, liquid drug formulations must sometimes be stored at 4° C., which makes it difficult for patients to transport such liquid drug formulations without specialized carrying devices.

For bolus injections of liquid drug formulations, pen injectors are utilized to control the dosage and to avoid certain problems of single-dose syringes. See, for example, Harris et al., U.S. Pat. No. 5,226,895. In such devices, patients are able to store several days worth of a liquid drug formulation within replaceable cartridges, and the quantity of injection is generally modulated by a screw plunger. However, these devices often require cold storage between uses, and the solutions or suspensions in the cartridges typically lack long term stability.

Various microcapsules, microparticles, and larger sustained-release implants have been used to deliver pharmaceuticals to patients over an extended period of time. For example, polyesters such as poly-DL-lactic acid, polyglycolic acid, polylactide, and other copolymers, have been used to release biologically active molecules such as progesterone and luteinizing hormone-releasing hormone (LH-RH) analogs, e.g., as described in Kent et al., U.S. Pat. No. 4,675,189, and Hutchinson et al., U.S. Pat. No. 4,767,628.

However, microcapsules and larger implants have certain drawbacks. First, the drug release or delivery profile of such implants cannot be precisely controlled over time, because the delivery rate is modulated only by polymer degradation characteristics. Second, even if these implants are designed to maintain a constant drug delivery rate, this rate is not precise and can change over time, resulting in an undesirable decrease or increase in the proper effective dosage. Third, there are few existing excipients or carriers that can be used effectively to provide the desired long-term, sustained-release, constant drug release profile. Moreover, as the amount of such carriers in a microcapsule or implant increases, their toxic effect on the body also increases.

The rate of delivery of drugs from microcapsules and implants is not very high, because any increase in the quantity of the active ingredient, e.g., the drug, typically causes a corresponding increase in the quantity of the carrier. The carrier plays two contradictory roles. First, it must protect and isolate the drug from body fluids. Second, the carrier must release the drug and control its delivery over an extended period of time into the very same body fluids. In addition, the total dosage that can be delivered is limited by the size of the implant.

Mechanical pumps are also used to provide long-term parenteral delivery of liquid drug compositions. In such pumps, a power source, such as an electric motor, inflated balloon, the vapor pressure of volatile liquids, a mechanical spring, or osmotic force, is used to expel the liquid drug formulation from the pump. However, these pumps require a large reservoir to provide infusion over a prolonged time period. Thus, their size is restricted by the volume of drug formulation to be delivered, i.e., they are either large in size to provide a sufficient drug volume, or small in size with a small drug volume. Furthermore, a large liquid volume requires a strong motor and energy source which further increases the size of these delivery systems.

Some pumps for liquid drug formulations are implantable, but because of their limited reservoirs, they are restricted to use with only certain drugs, and can deliver the drug formulation for only a limited time. Furthermore, some of the larger implantable pumps result in great discomfort to the patient. All of these factors make implantable pumps for liquid drug solutions inefficient, and single use, disposable pumps impractical.

SUMMARY OF THE INVENTION

The invention applies a new approach to solving problems of existing injection pens, pumps, microcapsules and implants by using new solid compositions including active ingredients that reduce the volume, compared to the same active ingredients in solution, by hundreds to thousands of times. The invention also covers devices specifically designed for use with these new solid compositions.

The invention features anhydrous, solid drug compositions for parenteral administration, e.g., as a long-term administration with a pump or other micro-mechanical system that dispenses the solid drug composition according to an adjustable delivery profile or as a pulsatile bolus delivery. The drug delivery profile is controlled by introducing predetermined portions of the entire composition, drug and carrier, if any, into the body. Accordingly, the carrier has no primary delivery role as in a sustained-release matrix, but is rather a texture and/or support agent. Once a portion of the drug composition contacts body fluids, the drug is quickly released from that portion of the carrier in the composition. This also allows the carrier to play secondary roles to improve drug activity, e.g., by coating, or targeting the drug.

In general, the invention features a device for the automatic delivery of an active ingredient, e.g., to an aqueous or air environment, according to an adjustable delivery profile, the device including a housing; a reservoir operatively connected to the housing and arranged to store a solid composition including the active ingredient; an actuator arranged within the housing to move the solid composition from the reservoir to a transit area, wherein the solid composition exits the housing at the transit area; a controller that acts on the actuator to adjust movement of the solid composition out of the housing according to the adjustable delivery profile; and a power source arranged to provide energy to the actuator and the controller. The device can be used to administer the active ingredient to an animal or human patient, e.g., by implanting the device into the patient.

The solid composition includes up to 90 percent, or preferably between 10 and 70 percent, by weight, of a carrier, e.g., a water-soluble carrier such as a cellulose derivative, hyaluronic acid, sugar, or gelatin, or a water-insoluble carrier such as a plastic, cotton, or silk.

The active ingredient in the solid composition is preferably a drug such as a polypeptide, protein, or peptide. Particular drugs include insulin, adrenalin, xylocaine, morphine, a corticoid compound, atropine, a cytostatic compound, estrogen, androgen, interleukin, digitoxin, biotin, testosterone, heparin, cyclosporin, penicillin, a vitamin, an anti-platelet activating factor agent, somatostatin, SOMATRIPTAN™, triptorelin, or diazepam.

When the device is designed for use in an aqueous environment, the housing is preferably filled with an oil, and includes an opening sealed with a flexible membrane arranged to flex into or out of the housing in response to ambient pressure around the device. A preferred device is designed to store and deliver the solid composition in the form of a filament, and the actuator preferably includes two rotating wheels arranged to contact and move the solid composition from the reservoir to the transit area.

The invention also features a method of automatically administering a drug to a patient according to a predetermined delivery profile by obtaining a device as described above loaded with a solid composition in which the active ingredient is a drug; programming the controller of the device to cause the actuator to move the solid composition to the transit area according to the predetermined delivery profile; bringing the transit area into contact with the body fluids of the patient, and providing energy to the controller and the actuator to move the composition from the reservoir to the transit area to deliver the drug to body fluids of the patient according to the predetermined delivery profile. The delivery profile can change over time.

In particular embodiments, the transit area is brought into contact with the body fluids of the patient by implanting the device into the patient, and the drug is administered to the patient continuously for over 3 months according to the delivery profile.

In addition, the invention features an elongate, anhydrous, solid drug composition, e.g., in the form of a filament or tape, for administration to a patient, the composition including a drug, e.g., insulin, and up to 90% of a carrier, e.g., a cellulose derivative, hyaluronic acid, sugar, or gelatin, wherein the composition has a cross-section of less than 0.5 mm, and wherein the drug and the carrier are selected and compounded in a proportion such that the drug is dispersed from the composition upon contact with bodily fluids and is distributed within the patient's bloodstream according to a blood level profile of the drug that is comparable to a blood level profile of the drug when administered in a liquid formulation.

Such a comparison of blood level profiles is easily made by taking blood samples at specific time intervals, e.g., 30 minute intervals over five hours, after the drug composition is administered, and measuring the concentration of the drug in the blood for each sample. The resulting profile is compared to a control administration of the same drug in a standard liquid formulation sampled at the same time intervals to determine whether the two profiles are "comparable," e.g., whether the drug concentrations in the blood for both the liquid and solid forms are within about 50% of each other at each time point after any initial peaks in concentration have stabilized.

In another embodiment, the composition has a surface area to drug ratio of at least 10 square millimeters per milligram of the drug. This ratio can be up to 30 to 60 square millimeters per milligram of drug for non-porous compositions and can be up to about 100 square millimeters for porous compositions.

The invention also features a method of making a solid drug filament by preparing a non-solid form of the drug, extruding the non-solid drug into an elongate filament having a cross-section of less than 0.5 mm and a surface area to drug ratio of at least 10 square millimeters per milligram of the drug, and solidifying the filament to form the solid drug filament. In particular, the non-solid form of the drug can be prepared by mixing a carrier with a sufficient amount of a solvent to form a gel and mixing the gel with the drug to form a homogeneous, non-solid form. The filament then can be solidified by removing the solvent. In an alternative embodiment, the non-solid form of the drug is prepared by mixing a carrier with the drug to form a mixture and heating the mixture to a temperature above a melting point of the carrier to generate the non-solid form, and the filament is solidified by cooling to a temperature below the melting point of the carrier.

The invention further features a device for the parental administration of a solid drug filament to a patient including a hollow housing; a reservoir, e.g., a bobbin, disposed within the housing to store a solid drug filament; an actuator arranged within the housing to move the solid filament from the reservoir to a delivery tube attached to one end of the housing, wherein the filament exits the housing through the delivery tube; and a plunger arranged to slide within the housing and the delivery tube, and to cut the solid filament into individual dosage units and move the units out of the housing through the delivery tube.

When this device contains the solid drug filament, the filament includes up to 90 percent, or between 10 and 70 percent, by weight, of a carrier such as a cellulose derivative, hyaluronic acid, sugar, or gelatin. The drug in the filament can be a polypeptide, protein, or peptide, e.g., insulin, or a growth-hormone or an analog thereof.

In particular embodiments, the actuator includes two rotating wheels arranged to contact and move the filament from the reservoir to the delivery tube, and the device can include an indicator to measure the amount of solid filament moved out of the housing.

The invention also features a method of parenterally administering a drug to a patient by obtaining a device as described above loaded with a solid drug filament; attaching a needle to the delivery tube; causing the actuator to move the filament from the reservoir to the delivery tube; inserting the needle into the patient; and moving the plunger to cut an individual dosage unit from the solid filament and move the unit out of the housing through the delivery tube and into the patient through the needle.

The term "analog" is used herein to cover naturally occurring, recombinant, and synthetic peptides, polypeptides, or proteins having physiological or therapeutic activity. In general, the term covers all derivatives and analogs of a biologically active peptide, polypeptide, or protein which exhibit a qualitatively similar agonist or antagonist effect to that of the unmodified peptide, polypeptide, or protein.

As used herein, a "water-soluble" carrier dissolves in water within about one day. A "water-insoluble" carrier does not dissolve in water, but still may be biodegradable and slowly disintegrate and disperse in an aqueous environment.

Unless defined otherwise, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

DETAILED DESCRIPTION

Figure 1:
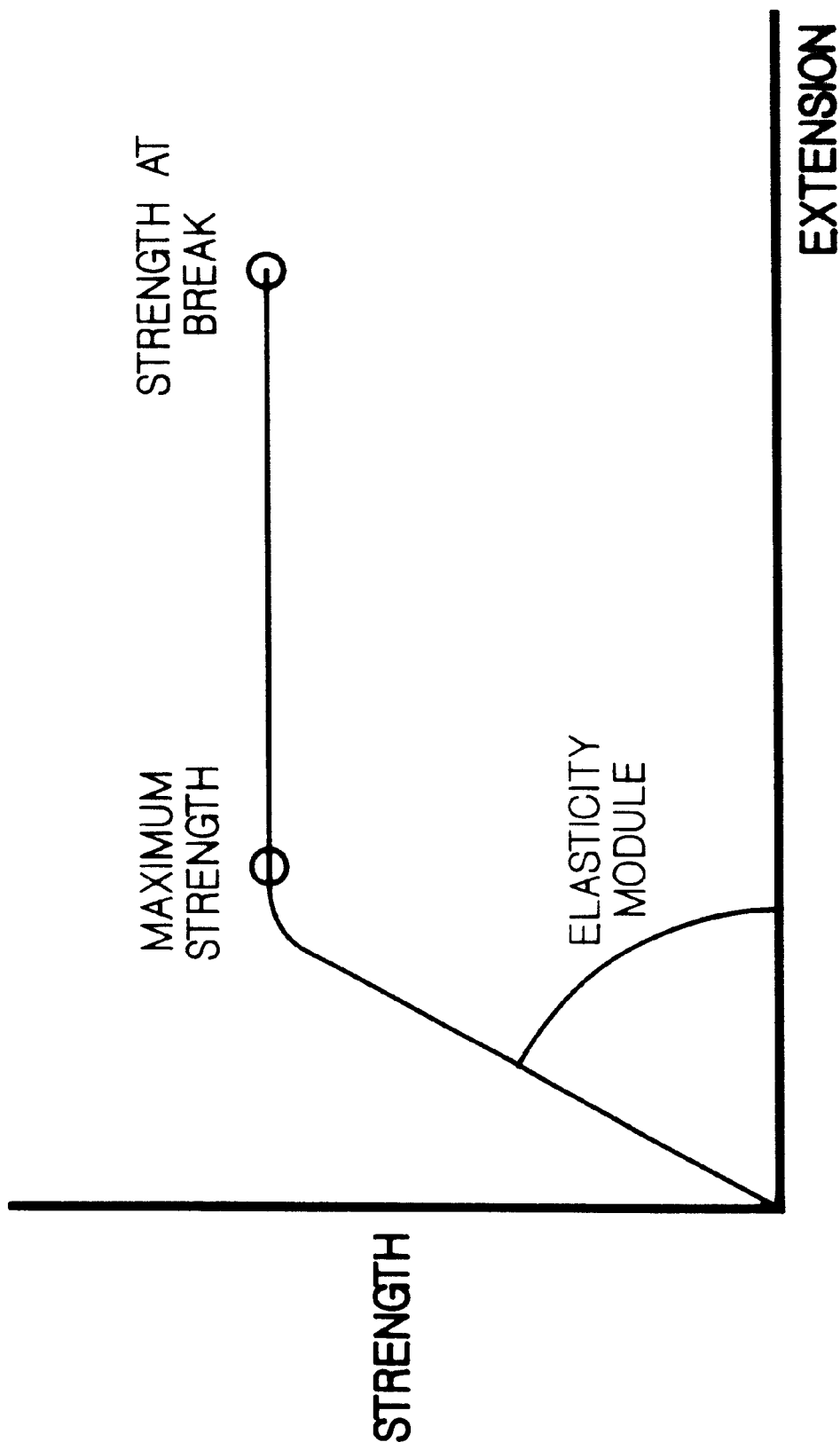
FIG. 1 is a graph of the strength v. extension of a solid drug filament.

The invention relates to miniature long-term delivery devices and pen-like injection devices specifically designed for use with new anhydrous, solid drug compositions. The long-term delivery devices, which are preferably implantable, dispense the solid drug compositions according to a predetermined delivery profile.

Solid Drug Compositions

The solid drug compositions include one or more drugs and one or more carriers, and are preferably in the form of a cylindrical filament or flat tape that is pliable enough to be handled and inserted into and dispensed from a delivery device, yet strong enough to withstand such manipulation. The cross-sectional shape and dimensions of these filaments or tapes must be consistent along their length, and small enough to allow for high precision in the delivery of the drug based on a given length of the filament or tape. These filaments have a diameter of, e.g., 0.1 to 0.5 mm, and preferably 0.2 to 0.3 mm, and can be one half to several meters in lengths. The tapes can be up to 0.1 mm thick and 2.0 to 5.0 mm wide.

The ratio of the surface area to the weight of the drug in the solid drug compositions, e.g., filaments or tapes, is also important to achieve a rapid dispersion of the drug from the composition once introduced into the bodily fluids of a patient. For a substantially non-porous solid composition this ratio should be at least 10 $mm^2$ of surface area per milligram of the drug in the solid composition, and can range up to 30 $mm^2$ to 60 $mm^2$ or more per milligram of drug. For a porous solid composition, the surface area can be much higher, because the pores add to the total surface area. In this case, the ratio can be in the range of 100 $mm^2$ per milligram. These ratios can be achieved by preparing the solid drug filaments as described below.

For example, a cylindrical filament with a diameter of 0.25 mm and a length of 10 mm has a total surface area of about 8.25 $mm^2$ (including the ends of the filament). If this filament contains, e.g., 0.165 mg of insulin, e.g., 40% insulin in a composition with a total weight of 0.4125 mg, the surface area to drug weight ratio is about 50 $mm^2$ per milligram.

The drug or drugs can be homogeneously distributed throughout the solid filament, or can be distributed only in discrete segments of the filament. Similarly, combinations of drugs can be homogeneously mixed throughout the composition, or distributed into separate discrete portions in a desired sequence to provide sequential delivery of different drugs. Sections of the composition without any drug can be interspersed between sections including a drug or drugs to provide intermittent or pulsatile delivery of the drug or drugs.

Drugs Suitable for Solid Drug Compositions

Certain drugs can themselves be formulated into a solid filament or tape without any carrier. For example, so-called "pro-drugs" are polymerized from hybrid molecules of a cross-linkable drug, e.g., a drug and a cross-linkable moiety, e.g., sugar or polyamino acid, e.g., polyarginine, derivatives. However, a typical drug composition will include at least 30% and up to 90% of the drug or drugs depending on the physical characteristics of the carrier and the resulting filament or tape. Preferably the composition contains at least 50% of the drug.

Even when a carrier is used, an advantage of the solid drug compositions is that they minimize the total amount of carrier introduced into the patient. In particular, the drug compositions preferably include less than 50% by weight of a carrier. Many liquid drug formulations include organic solvents or other additives, e.g., to change the pH to force the drug to dissolve in the solution. Such solvents and additives are usually toxic to the patient, even in small amounts, and thus, it is advantageous to minimize their use.

The invention also avoids formulation and solubility problems of liquid drug solutions. Therefore, the drug compositions can include any one or more of a wide variety of drugs, even those which are insoluble or otherwise incompatible with standard liquid formulations, because the drug, e.g., in particulate form, can be merely dispersed in the carrier to form a suspension without dissolving the drug. The resulting homogenous mixture is then solidified. As a result, drugs that are insoluble, or that are otherwise incompatible when in solution, can be easily incorporated into a solid drug composition.

Another advantage of the invention is the increased stability of the drug in the solid composition. Drug solutions are often difficult to keep stable for prolonged periods of time. The anhydrous, solid drug compositions largely avoid this problem. Moreover, solid compositions are not subject to the same sheer forces and turbulence that break down proteins and peptides in solution. Thus, the drug or drugs in the solid drug compositions are stable for long periods of time compared to the same drugs in a liquid formulation.

Drugs that can be used in the solid drug compositions include polypeptides such as growth hormone (GH), growth hormone releasing peptide (GHRP), growth hormone releasing factor (GRF), epidermal growth factor, interferon, insulin, somatostatin, bombesin, calcitonin, calcitonin gene related peptide (CGRP), amylin, parathyroid hormone (PTH), parathyroid hormone related peptide (PTHrp), gastrin, gastrin releasing peptide (GRP), melanocyte stimulating hormone (MSH), adrenocorticotrophic hormone (ACTH), luteinizing hormone (LH), luteinizing hormone-releasing hormone (LH-RH), cytokinases, sorbine, cholecystokinin (CCK), glucagon, glucagon-like peptide (GLP), gastrin, enkephalin, neuromedin, endothelin, substance P, neuropeptide Y (NPY), peptide YY (PYY), vasoactive intestinal peptide (VIP), pituitary adenylate cyclase activating polypeptide (PACAP), bradykinin, thyrotropin releasing hormone (TRH), or derivatives, fragments, analogs, agonists, or antagonists of any of the foregoing.

Preferably, the drug is used for diabetes, inflammation, oncology, cardiology, hormone therapy, gynecology, immunology, metabolism, or maturation, or as a vaccine. Examples of such drugs include insulin, adrenalin, xylocaine, morphine, corticoid compounds, atropine, cytostatic compounds, estrogen, anti-PAF (platelet activating factor) agents such as ginkolides (e.g., BN 52021 or BN50730, Beaufour Ipsen, France), androgen, interleukin, digitoxin, biotin, testosterone, heparin, cyclosporin, penicillin, vitamins, SOMATRIPTAN™, or diazepam.

Carriers Suitable for Solid Drug Compositions

The nature of the drug composition depends upon the type of delivery device to be used. The drug composition can contain any of a large number of carriers, with only minor, if any, limitations in terms of delivery properties or toxicity, because of the small carrier volume. When the drug composition is intended to be dispensed into the body from the delivery device, the carrier should be water-soluble. Suitable water-soluble carriers include such polymers as hyaluronic acid, cellulose, e.g., hydroxy propyl methylcellulose (HPMC), carboxyl methylcellulose (CMC), and hydroxy ethylcellulose (HEC), polyalcohols such as mannitol, sugars, e.g., dextrose, mannose, or glucose, and starches.

When the drug composition is intended to be merely exposed to bodily fluids, but not dispensed directly into the body from the delivery device, the carrier should be substantially water-insoluble, but preferably biodegradable to allow the drug to easily be released from the carrier. Examples of suitable water-insoluble polymers include L-lactic acid, D-lactic acid, DL-lactic acid, glycolide, glycolic acid, and any optically active isomers, racemates, or copolymers thereof. Non-biodegradable, water-insoluble carriers are also useful, and include silicon, nylon, polypropylene, polyethylene, silk, or cotton. Other suitable water-insoluble carriers include fatty acids, collagens, lipids, and waxes.

Method of Making a Solid Drug Compositions

A carrier, e.g., HEC, HPMC, or hyaluronic acid, and water are added to a container, e.g., a 10 ml syringe which was previously covered at the bottom with a stopper. The two ingredients are mixed, e.g., using a spatula, to homogeneity. Once a gel is formed and allowed to reach structural equilibrium, e.g., after about 24 hours, the gel is mixed with the desired drug or drugs in another container, e.g., a 2 ml plastic syringe. If no carrier is used, the drug itself is mixed with water. The resulting gel/drug mixture, or drug/water paste, is kneaded to homogeneity, e.g., with a spatula.

The mixture is then transferred to an extrusion device, e.g. a stainless steel syringe, with an extrusion nozzle, e.g., a hollow cylindrical needle attached to the syringe if a cylindrical filament is desired. Other nozzle shapes can be used to create flat tapes of the gel/drug mixture or the drug/water paste. The amount of drug per amount of gel can be varied in separate batches of gel and then added to the extrusion device in sequence to create a filament that will dispense different drugs in the desired sequence. Similarly, batches of gel without any drug can be interspersed between batches of drug containing gel to create a filament that provides intermittent drug delivery.

The gel/drug mixture is extruded into a drying chamber as a continuous cylindrical filament or flattened tape, depending on the cross-sectional shape of the extrusion nozzle. For drying, the barrel of an extrusion syringe can be connected to the drying chamber of a mini-spray dryer (BUCHI 190, Buchi Laboratoriums Technik AG, Switzerland), and the extruded filament or tape is collected, e.g., onto a sieve placed at 10 cm under the exit of the needle, so as to avoid stretching of the filament after extrusion. The drying system is heated, e.g., to 40° C., and connected to an air blower. The filament is therefore partially dried immediately upon exiting the needle, which also tends, to avoid undesired stretching. The filament is further dried under vacuum until all water is removed, e.g., for 24 hours.

The filament can also be dried under continuous vacuum from the moment of extrusion into a glass vessel. The filament can also be collected into a coagulation bath and then dried to avoid stretching.

Other standard techniques, such as fusion extrusion or wet or dry spinning, also can be used to create the solid drug filaments. All of these techniques involve moving a non-solid mass of material through an orifice with a particular shape that produces an elongated filament with a desired cross-section. This filament can be directly dried or otherwise solidified, or can be stretched and then solidified. The material is made non-solid by heating or adding a solvent, and is returned to a solid state by cooling or removing the solvent by, e.g., evaporation, freeze drying, or vacuum drying, respectively.

To determine the mass percentage of drug in the filament, samples of a specific length are taken, the total amount of drug is removed from the filament, e.g., by acetic acid 0.1% in water or any other appropriate drug solvent, and is measured using standard HPLC methodology. For example, when the drug is insulin, a chromatograph column of Kromasil-C8 5 µm 25×0.46 cm can be used. The mobile phase is an isocratic mixture of acetonitrile and 0.1% triethylamine in 0.2M $Na_2SO_4$, pH of 2.3. The various drug components are detected under UV at 220 nm. The solvent for the sample is 0.05N HCl and 0.2 mM cetyl-tri-methyl-ammonium bromide (Sigma).

After drying is complete, the tensile strength of the drug-containing filaments or tapes, is measured to determine its propensity to break. This method involves incrementally stretching a filament until it breaks and recording this requisite minimum force. Breakage strength, elasticity, and other mechanical parameters of the filaments or tapes can all be measured, e.g., with a Universal Testing Instrument (Lloyd 100R, Lloyd Instruments, England). To proceed with this analysis, ten equal lengths of the same filament are tested. Each filament length is individually tested on the device to determine a strength/extension ratio. Elasticity module, strength at breaking, maximum energy required for breaking, and other mechanical properties can be calculated from a graph (FIG. 1).

The weight/length ratio is also calculated for each of ten equal lengths of ten different filaments. A specific filament is utilized only if the Relative Standard Deviation (RSD) of this ratio is less than 1%. This RSD equals the (standard deviation of the weight/length ratio÷mean)×100, so it is a measure of the uniformity of the weight/length ratio. To ensure uniformity of a given filament, which may be one or more meters in length, samples are taken at the beginning and the end of the filament and compared. These same samples are also used for the HPLC drug content analysis.

The precise dosage of the filament can then be calculated for a given length of the filament. For example, a cylindrical filament of 0.2 mm diameter, loaded with 45% SOMATULINE™ and 55% HEC, will provide a dosage of 0.125 mg for each 1 cm of length dispensed into the bodily fluids. In another example, pure insulin, e.g., recombinant human insulin, provides about 26 to 28 Insulin Units (IU) per mg depending on purity. Therefore, a filament having a diameter of 0.3 mm, loaded with 50% insulin and 50% hyaluronic acid will provide a dosage of 0.27 mg or about 7.3 IU per cm. Such solid insulin filaments can then be used to administer the required dosage, e.g., 20 to 50, and even up to 200 IU per day, merely by administering the proper length of filament to the patient. Furthermore, at body temperature, such an insulin filament should remain stable for several months to over a year.

Once the above tests are satisfied and the precise dosage per unit length is calculated, each filament is loaded into a delivery device as described below.

EXAMPLES

Solid Insulin Compositions

The present solid drug compositions and devices are well-suited for insulin therapy. The devices are small enough to be implanted subcutaneously or intraperitoneally and are designed to dispense precise amounts of a drug over prolonged periods of time. The solid drug filaments are stable and provide a high dosage per unit volume. Solid filaments of insulin and HEC as a carrier were manufactured according to the method described above.

Human recombinant insulin (HRI) was mixed with a HEC gel to provide a solid filament containing 40% insulin by weight. The above protocol was performed by mixing 1.0 g of HEC and 9.0 g of water. 0.26417 g of the resulting gel was added to 0.02648 g of HRI. The mixture was extruded through a 2.3 mm syringe (0.3 mm internal diameter needle) with a Harvard syringe pump. The filaments were extruded and dried under vacuum for 24 hours, and were examined for homogeneity, stability, and solidity. These filaments provided a good precision of insulin delivery at a dosage of 0.184 mg insulin (4.96 IU)/cm.

Figure 2:
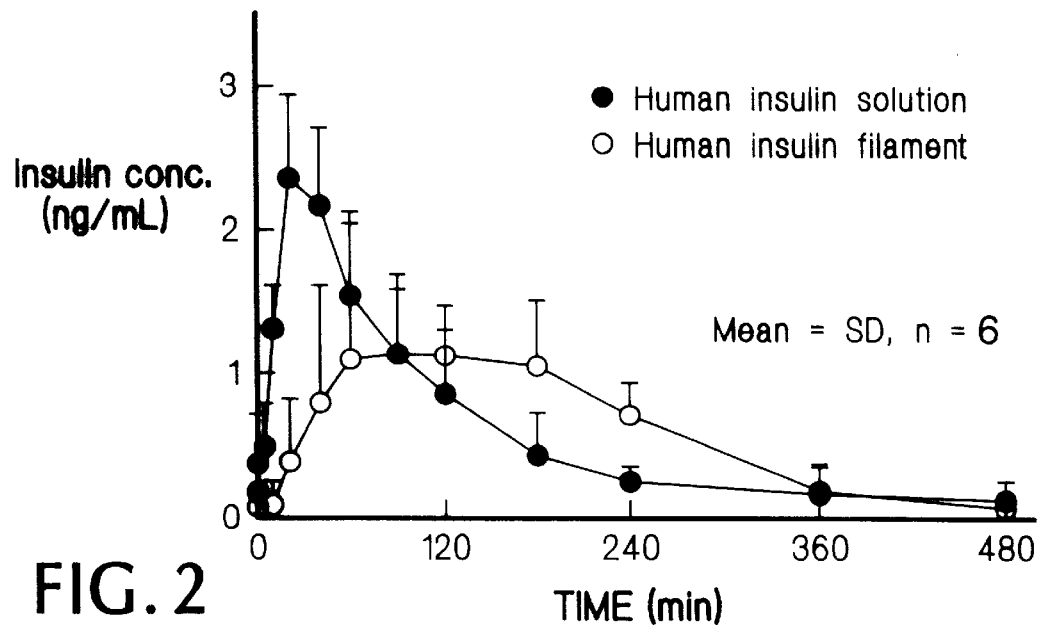
FIG. 2 is a graph showing the blood level of insulin in beagle dogs due to injections of a solid insulin filament (40% insulin) or a standard liquid insulin formulation.
Figure 3:
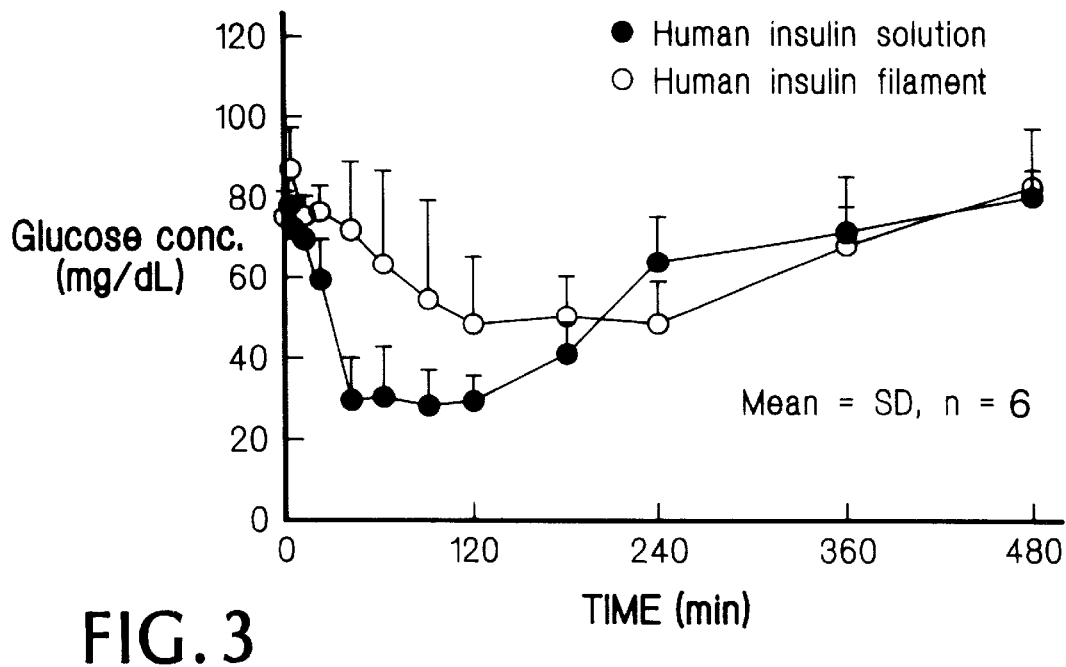
FIG. 3 is a graph showing the blood level of glucose in beagle dogs due to injections of a solid insulin filament (40% insulin) or a standard liquid insulin formulation.

The filaments were then tested in terms of biopharmaceutical activity by implanting given lengths of filaments into beagle dogs subcutaneously. The hypoglycemic effect of the filaments were measured and compared to the same dosage administered as a liquid insulin solution. As shown in the graphs of FIGS. 2 and 3 the solid filaments (O) were found to have essentially the same effect on insulin level (FIG. 2), and to be as efficient in lowering the blood glucose level (FIG. 3) as the standard liquid insulin formulation (●). FIGS. 2 and 3 show the mean results of six different dog tests.

Similarly, bovine pancreas insulin (BPI) was mixed with HEC to form a solid drug composition containing 50% insulin. The above protocol was performed by mixing 1.5 g of HEC and 8.5 g of water. 0.37733 g of the resulting gel was added to 0.05643 g of BPI. The mixture was extruded through a 2.3 mm syringe (0.3 mm internal diameter needle) with a Harvard syringe pump. The filaments were obtained by extrusion and drying under vacuum for 24 hours, and provided a good precision of insulin delivery at a dosage of 0.206 mg insulin (5.56 IU)/cm.

Solid SOMATULINE™ Compositions

Filaments were also made with a somatostatin analog, SOMATULINE™ (BIM 23014C, Biomeasure, Milford Mass.) and HEC or hyaluronic acid as the carrier to produce a solid composition containing 50% SOMATULINE™.

The above protocol was performed by mixing 1.500 g of HEC and 8.500 g of water. 0.42250 g of the resulting gel was added to 0.06395 g of BIM 23014. The mixture was extruded through a 2.3 mm syringe (0.3 mm internal diameter needle), collected, and dried under vacuum for 24 hours. The dried filament contained 0.107 mg of BIM 23014/cm (weight percentage 50% HEC and 50% BIM 23014).

Figure 4:
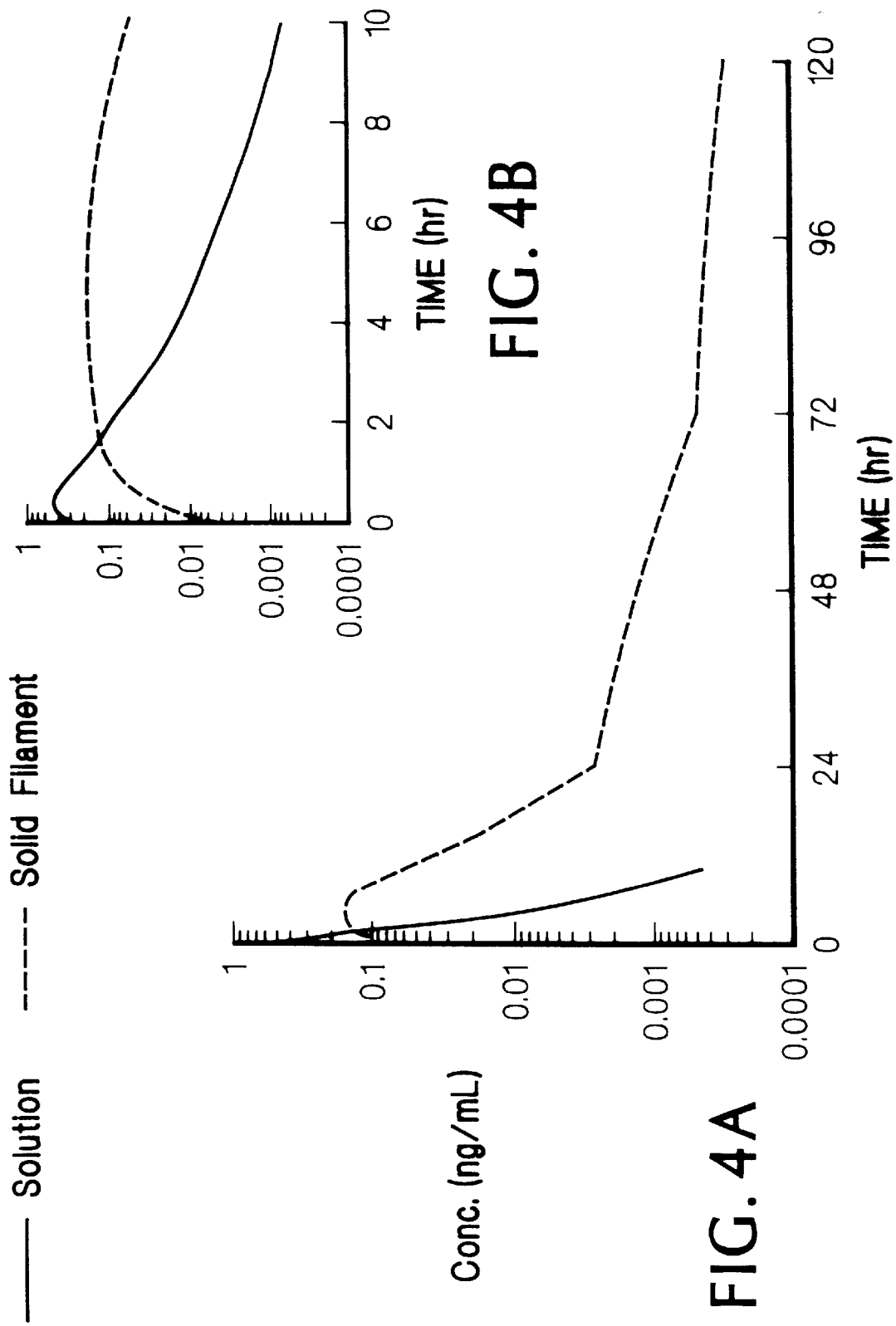
FIGS. 4A and 4B are graphs showing the blood level in a dog of a somatostatin analog, SOMATULINE™ (BIM-23014C, Biomeasure, Milford Mass.) after implantation of a solid filament compared to a liquid solution of BIM-23014C. The graph of FIG. 4A shows the blood level over 120 hours, whereas the graph of FIG. 4B is more detailed and shows the SOMATULINE™ blood level over 10 hours.

The filaments were tested for pharmacokinetics and compared to liquid infusions of the same dosage of SOMATULINE™ in dogs. The results are shown in the graphs in FIGS. 4A, 4B, and 5. As shown in FIGS. 4A and 4B, the solution formulation provided an initial blood concentration of SOMATULINE™ of about 0.5 ng/ml. However, the blood concentration decreased to less than 0.1 ng/ml within about 2 hours, to less than 0.001 within about 8 hours, and to about 0.0005 ng/ml in less than 12 hours. On the other hand, the blood concentration of SOMATULINE™ provided by the solid drug filament was at an almost constant level over 0.1 ng/ml for the first 10 hours, declined to about 0.002 ng/ml within 24 hours, and declined further to 0.0005 ng/ml by 72 hours.

Figure 5:
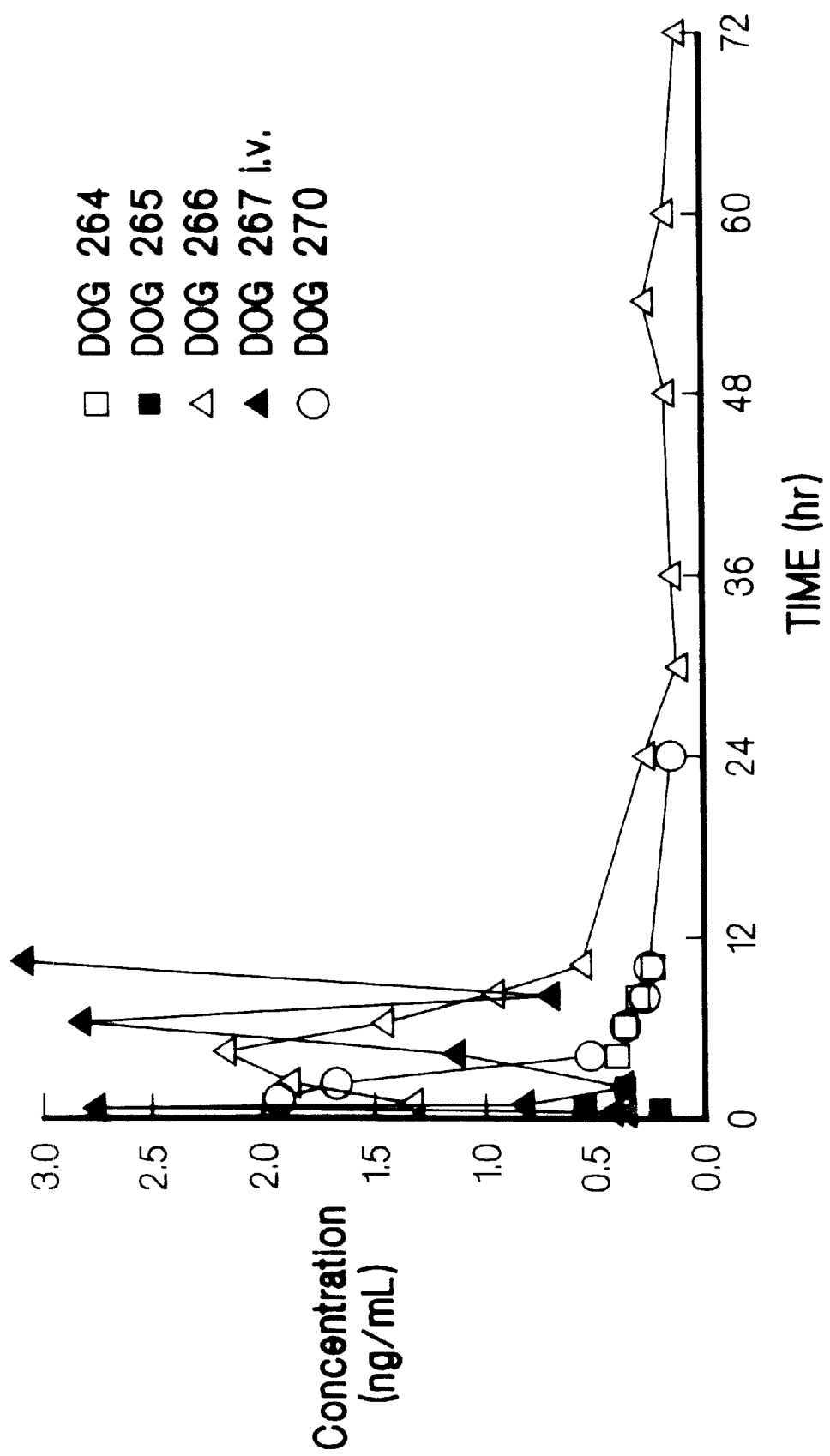
FIG. 5 is a graph showing the blood level of SOMATULINE™ after implantation of solid filament into five different dogs.
Figure 6:
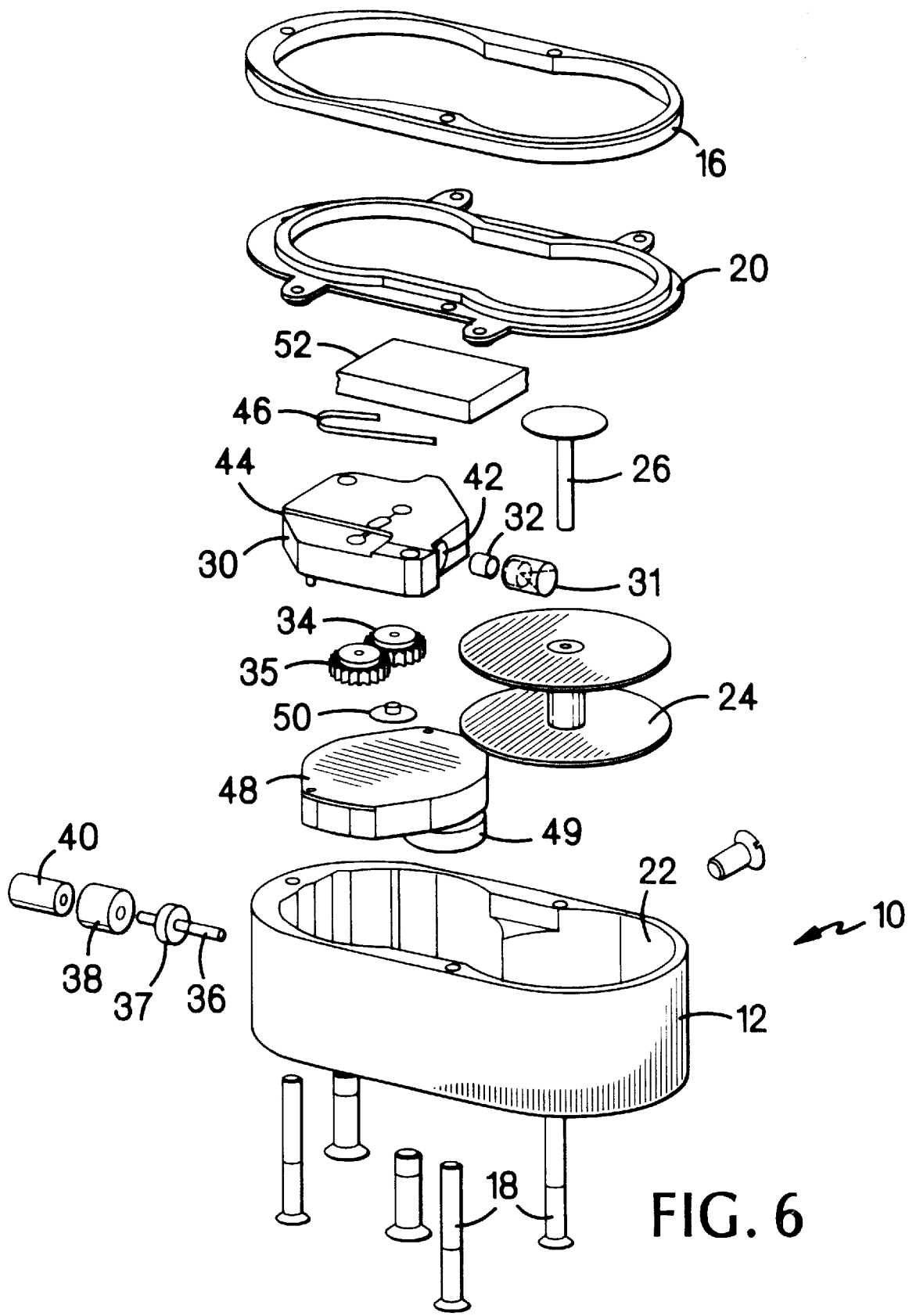
FIG. 6 is an exploded view of an implantable solid drug composition filament delivery device.
Figure 7:
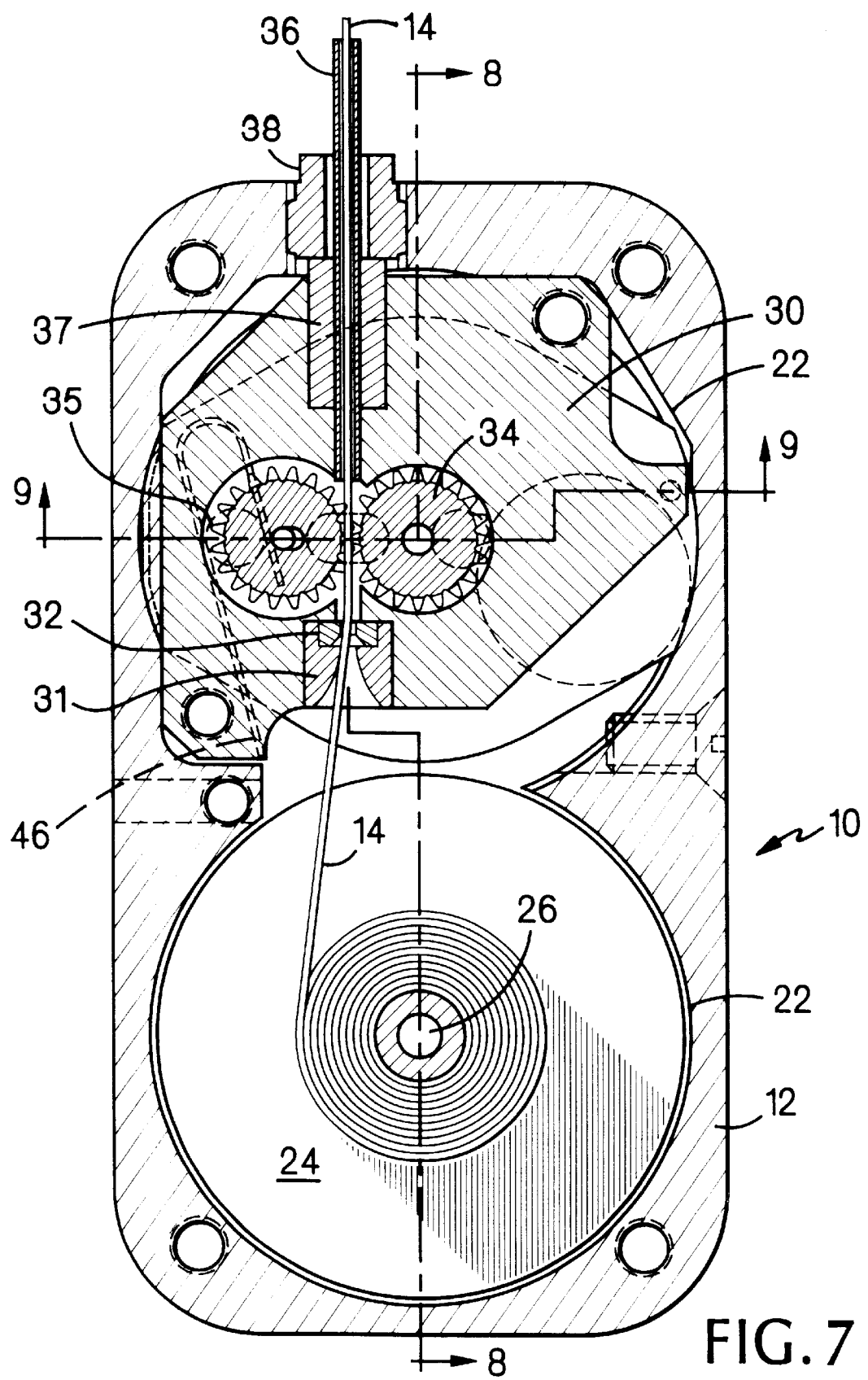
FIG. 7 is a top view of the delivery device of FIG. 6 in partial cross-section along section line 7—7 in FIG. 8.
Figure 8:
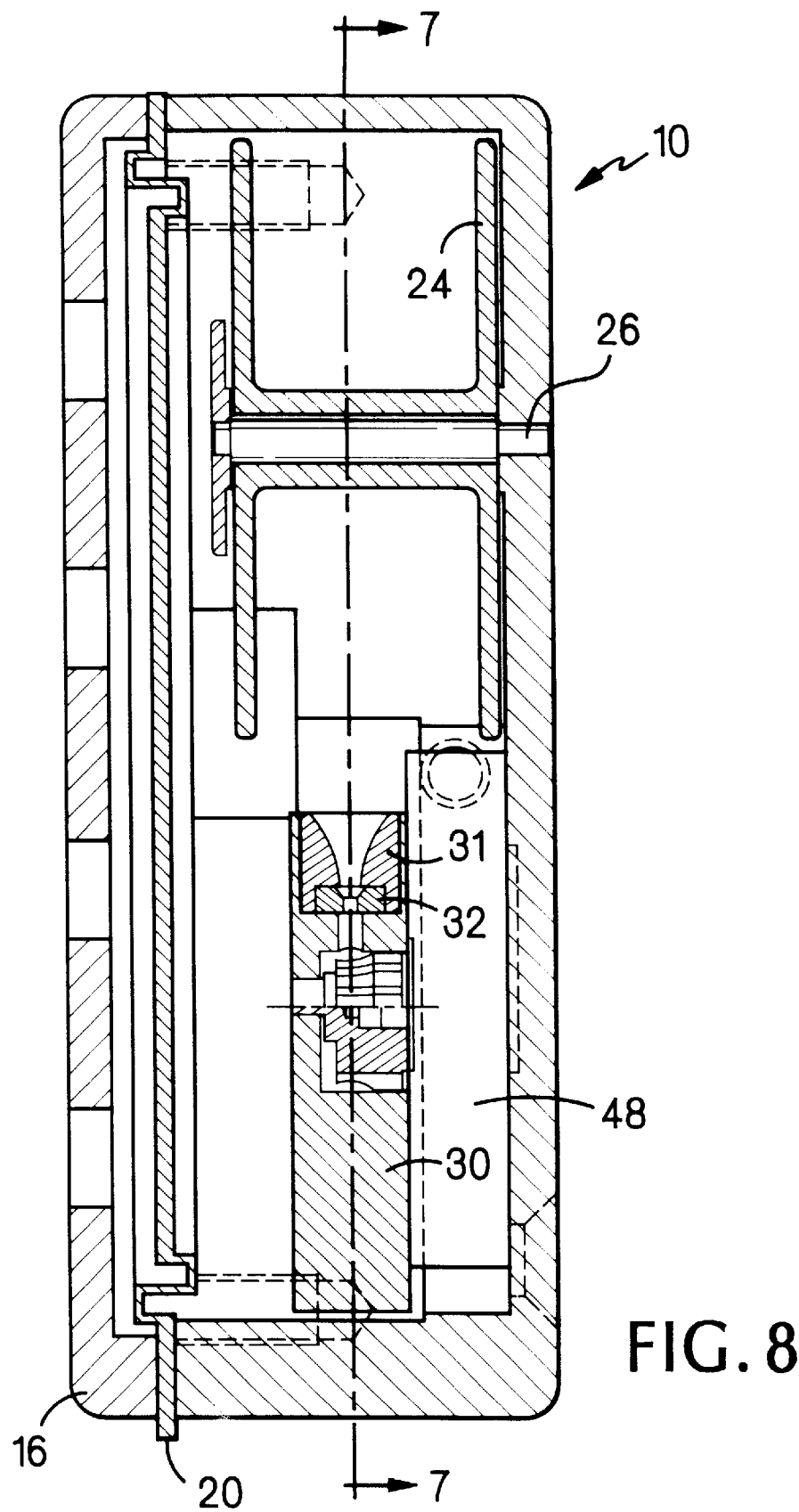
FIG. 8 is a side cross-sectional view of the delivery device of FIG. 6 along section line 8—8 in FIG. 7.
Figure 9:
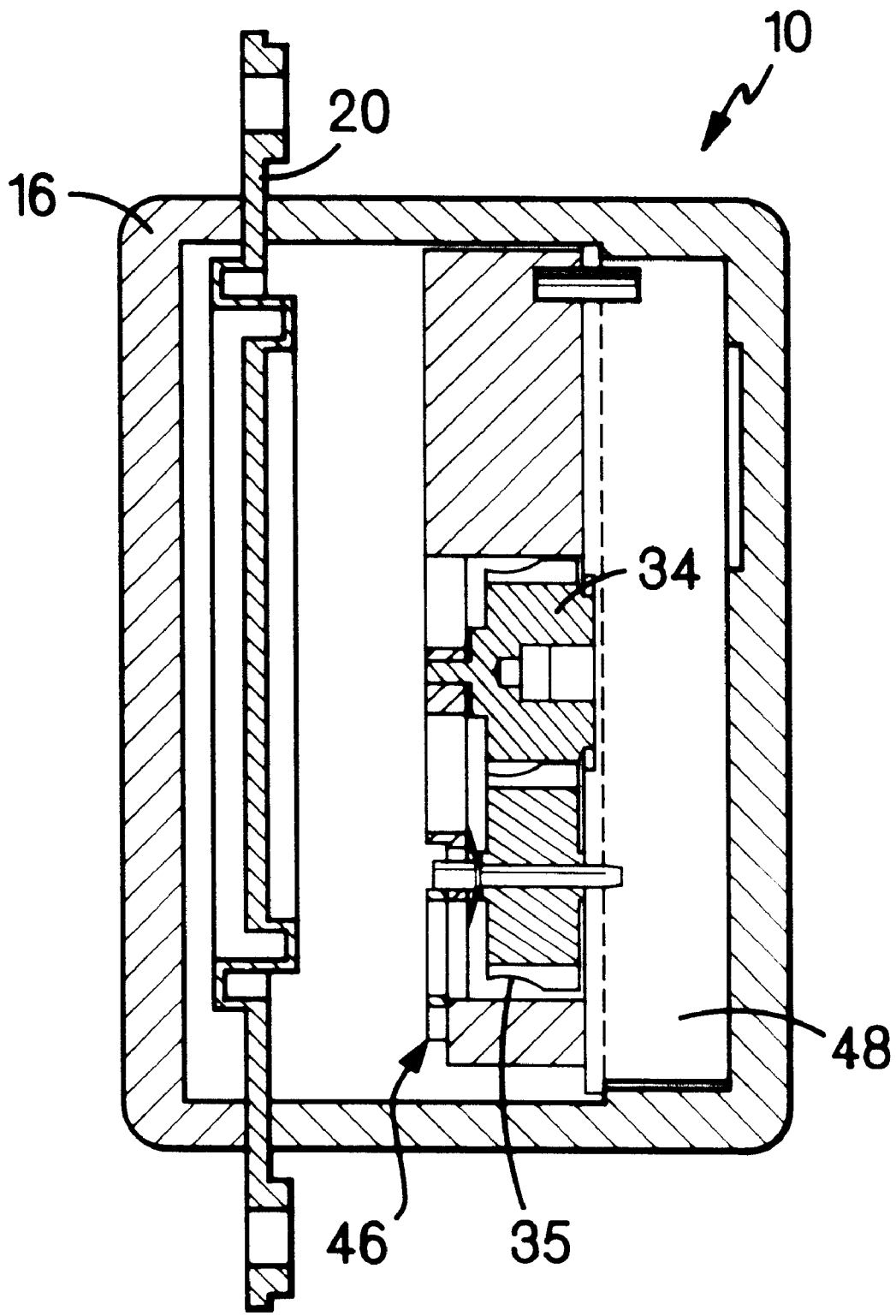
FIG. 9 is an end cross-sectional view of the delivery device of FIG. 6 along section line 9—9 in FIG. 7.

Similarly, FIG. 5 shows the results of administrations of SOMATULINE™ filaments to five different dogs. The different symbols in the graph, i.e., square, circle, triangle, represent different dogs. Dog number 267 was injected intravenously, whereas the other dogs were injected subcutaneously.

Solid LH-RH Agonist Analog Compositions

Filaments were also made with a synthetic peptide agonist analog of LH-RH, triptorelin acetate (Shally et al., U.S. Pat.

No. 4,010,125), and HEC as the carrier, to produce a solid composition containing 50% triptorelin.

The above protocol was performed by mixing 1.500 g of HEC and 8.500 g of water. 0.19778 g of the resulting gel was added to 0.02968 g of triptorelin acetate. The mixture was extruded through a 2.3 mm syringe (0.3 mm internal diameter needle), collected, and dried under vacuum for 24 hours. The resulting filament contained 0.216 mg triptorelin/cm (weight percentage 50% HEC and 50% triptorelin).

An Implantable Drug Delivery Device

An important advantage of this invention is the miniaturization of the drug reservoir compared to standard liquid drug dispensing devices. Solid drug compositions occupy a very small volume in comparison with liquid drug formulations. With many drugs, this reduces the total volume by hundreds or thousands of times, and thus allows the present devices to be much smaller than prior implantable liquid drug pumps.

The miniaturization of the drug reservoir is highly compatible with miniature motors, electronics, and batteries, and results in a very small total size and volume of the device. The device motor and movement are lighter and more energy efficient than comparable motors for liquid pumps because of the greatly reduced drug volume. Whatever the drug, one can make a device with a duration and delivery profile adapted to a specific disease.

The delivery device will always contain the following elements: 1) a solid drug composition with or without a carrier as required for the specific delivery system which is protected from the surrounding environment, e.g., the bodily fluids; 2) an actuator capable of delivering this drug composition to the patient; 3) a power source; 4) a transit or contact area where the drug is released from the composition to the environment outside of the device; and 5) a housing to enclose all, or at least the liquid-sensitive, of these parts and the drug composition, fitted together in a specific manner for a specific remedy and/or therapy.

With reference to FIGS. 6 to 9, device 10 includes a housing 12, which encloses all of the other parts of the device and the solid drug composition, which is in the form of a filament 14, and prevents contact of these parts with the environment outside the device, e.g., bodily fluids. Housing 12 may be machined or molded from a suitable heat resistant, chemically inert, sterilizable, rigid material, e.g., polyvinylchloride, polycarbonate, TEFLON®, POLYSULFONE® (AMOCO), stainless steel, or titanium. The housing may be transparent to facilitate the determination of whether filament 14, is properly feeding through the device. The external dimensions of the housing may be about 4 cm by 2 cm, and 1 cm high, or 3 cm in diameter by 1 cm in height when in cylindrical form.

Housing 12 is sealed watertight by means of a cover ring 16, and screws 18. The cover ring secures a cover 20, which is preferably a flexible membrane molded from, e.g., silicone, rubber, or a biocompatible elastic. This cover or membrane is in the general shape of opening 22 in the housing. The cover 20 is placed over the opening between the housing 12 and cover ring 16, which is also in the shape of the opening. The ring 16 is attached to the housing with screws 18 to create a watertight seal around the opening in the housing. If the cover is a membrane, it can flex in or out of the housing as a result of changes in the ambient pressure or pressure within device 10 once it is implanted into a patient. Pressure fluctuation within the device may result, e.g., from the decrease in pressure within the device when the drug composition is released from the device.

Housing 12 encloses a reservoir for the solid drug composition filament, which in this embodiment is a removable bobbin 24. Filament 14 is wrapped around the bobbin before the bobbin is inserted into the housing. The bobbin is secured in the housing by a bobbin pin 26. The filament is initially fed from the bobbin, into actuator 30 which includes feeder cylinders 31, 32, and gear wheels 34, 35. The feeder cylinders direct the filament between two wheels 34, 35 which contact and pull the filament forwards between them and feed the filament out of the device through a transit assembly (36, 37, 38, 40). This transit assembly fits into an opening in the housing like a cork in a bottle.

The feeder mechanism includes two cylindrical members. The first member 31 is hollowed in a conical fashion at the proximal end, e.g., the end that filament 14 first enters, to facilitate entry of the filament into the actuator. The distal end of member 31 is hollowed such that the internal diameter is the same as the outer diameter of the second member 32. Other feeder mechanisms can be easily adapted for this device.

Actuator 30 houses the feeder mechanism and also supports gear wheels 34, 35 preferably manufactured from stainless steel or plastic. These wheels can also be smooth-surfaced wheels or rollers, e.g., of rubber or plastic, without gear teeth, as long as they can contact and move the solid drug composition filament from the reservoir through the actuator, and out of the device. The actuator has two openings 42, 44. The first opening 42 provides the entrance to the actuator through the proximal end of the first cylindrical member 31. The second opening 44 is fitted with the transit assembly (36, 37, 38, 40). The two gear wheels 34, 35 are positioned between the two openings 42, 44, and are arranged to contact filament 14 between them. The wheels rotate in opposite directions such that the filament is moved between them and fed out of the device through the transit assembly. The pressure that the wheels place on the filament is regulated by spring 46 (shown in dashed lines in FIG. 7) which forces the two wheels towards each other.

The power supply for the device in this embodiment is an electrical motor 48 powered by a battery 49, e.g., a lithium battery that is designed to provide electricity for several years. The motor rotates an axle which engages a small gear 50 which in turn engages one of the two gear wheels 34, 35. Gear 50 causes wheel 34 to rotate, which in turn causes the second wheel 35 to rotate in the opposite direction. The motor can be an inexpensive one-step watch movement, which includes a motor and a gearbox, and which is usually less than 2.5 cm by 5 mm. For example, a circular movement can be 2.5 by 0.3 cm, and a rectangular motor can be 1.8 by 1.5 by 0.3 cm. In the case of a watch motor, the power can be transmitted to the gear wheels by either the hour or minute hand axles.

Suitable watch movements include F. E. 6220 and 6230 (France-Ebauches, S. A.)(size 6 ¾, 8), Ronda Harvey (10 ½), Ronda 313 (11 ½), and ISA 1198 (11 ½). Other possible motors include continuous current motors, e.g., Maxon DC motor (2.8 to 12 mm diameter) or Arsape AM 15–24 or AM 10–20 motor, or stepper motors, e.g., Arsape single phase stepper motors P130–S130 or P141, or MMT two phase stepper motors.

Preferably, the motor interacts with the actuator through a gear box or a transmission which reduces the rotation speed and/or increases power. Other types of motors may be used, e.g., a spring-powered or shape memory alloy-powered mechanical motor, or an osmotically or electrochemically driven motor, as long as the power can be converted into a force that moves the filament from the bobbin to the transit assembly.

The transit assembly includes four members: a guide tube 36, a support 37, a screw 38 to connect the guide tube to housing 12, and a cap 40 which protects the device and must be removed prior to use. The inner diameter of the transit guide tube 36 is only slightly larger then the outer diameter of filament 14. The inside of guide tube 36, and preferably the entire housing, is filled with a biocompatible oil to insure that the housing remains watertight. Suitable oils include silicon oil, Dow Corning 344 medical fluid, Miglyol 812 Dynamit oil, castor oil, isopropyl myristate, ethyl oleate, or injectable olive oil. The oil prevents aqueous liquids, e.g., bodily fluids, from entering the housing through the transit assembly. In other embodiments, the oil is contained only within a small reservoir in the transit assembly.

The delivery profile of the drug, i.e., the dosage of the drug or drugs delivered by the device over a set period of time, is controlled by a combination of the solid drug composition itself, and a control mechanism 52 arranged within the device. A varied or changing delivery profile is desirable in the treatment of diseases in which the requirement for one or more drugs varies throughout the day. A good example is diabetes, in which a basal dose of insulin must be supplemented by bolus doses, e.g., at meal times.

The delivery profile can be varied in three ways. First, the drug composition filament is precisely manufactured, e.g., extruded, to contain a specific known amount of drug per unit length of the filament. The amount of drug can be varied along the length of the filament, and various drugs can be mixed within the same segment of filament or included separately in sequential segments of the filament as described above. Thus, a precise delivery of drug or drugs can be achieved by dispensing the filament into the body of the patient at a fixed rate, with any desired variation in delivery profile being based solely on the nature of the filament. In such a device, the electrical control mechanism 52 can be very simple, and needs only to turn the motor on and off, and maintain it at a constant speed. In addition, all such mechanisms should include safety features, such as a default "off" position, to avoid accidental dispensing of the drug.

Second, the delivery profile can be varied by changing the rate at which the filament is dispensed from the device. This can be accomplished by changing the speed at which motor 48 causes wheels 34, 35 to rotate. For example, the device may be controlled to dispense the filament only during certain hours of the day, or at one rate for certain hours, and at another rate during other hours. In such an embodiment, the electrical control mechanism 52 is more complex, but such controllers and related circuitry are known in the art as described below.

Third, the delivery profile can also be varied by a combination of variable drug loading in the filament, and variable delivery rate. For example, the rate of delivery can be changed by altering the speed at which the wheels rotate, and the type of drug being dispensed can be altered by the type of filament loaded into the device.

The control mechanism 52 preferably includes an integrated circuit or microprocessor and related circuitry which controls the motor and is pre-programmed to the desired delivery profile, or is arranged with a receiver to receive, e.g., radio, control signals from a programmer device located outside of the patient to allow for alterations in the delivery profile over time. Such microchips and microprocessors and related circuitry are known in the art and can be easily adapted to control an electric motor for use in the present devices. Examples of such electrical control mechanisms and telemetry systems are described, e.g., in U.S. Pat. Nos. 5,049,141 and 4,265,241. The power supply for this controller could be battery 49, or an additional, separate battery.

EXAMPLES

Figure 10:
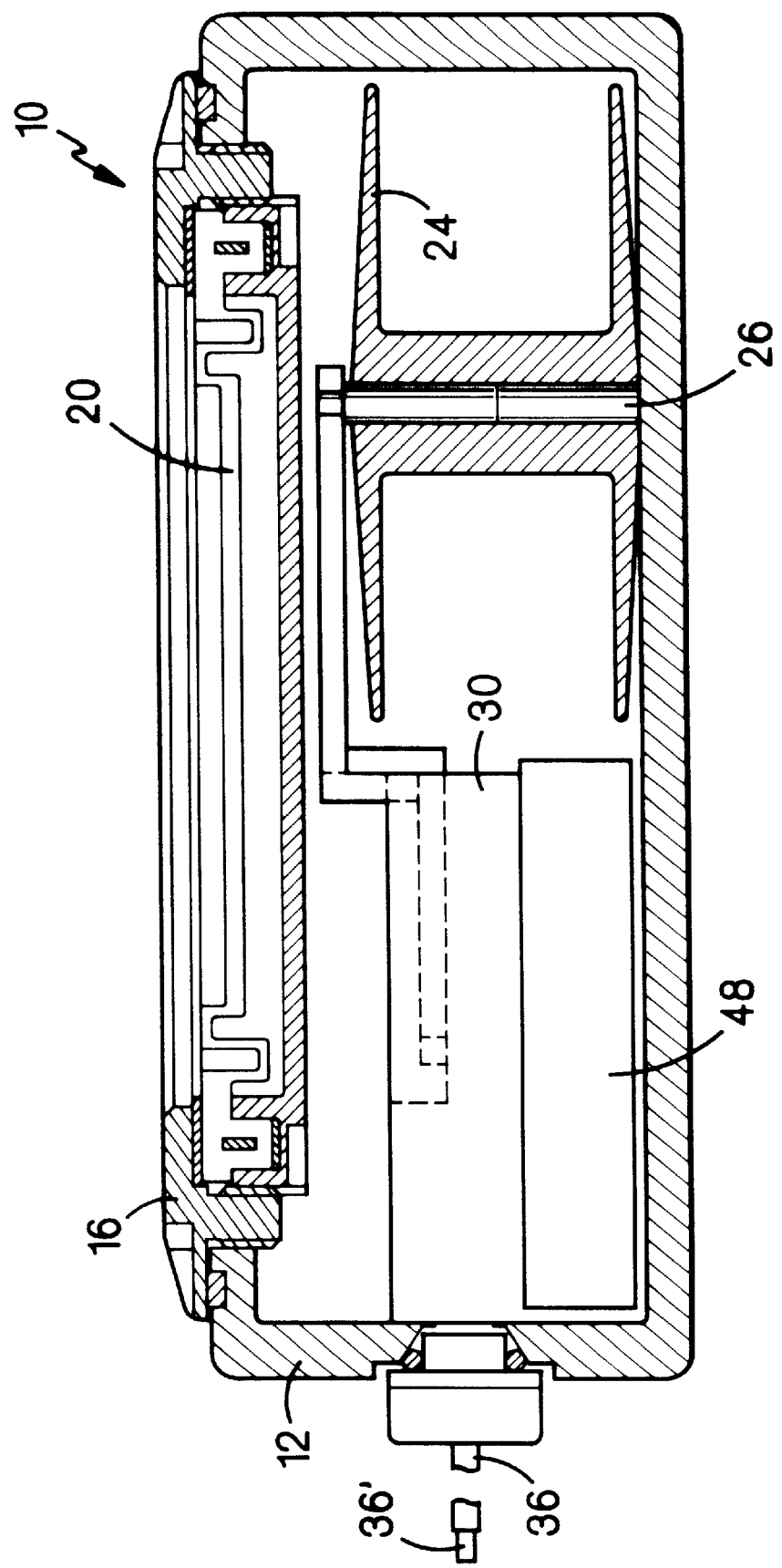
FIG. 10 is a side cross-sectional view of a cylindrical implantable solid drug composition filament delivery device.
Figure 11:
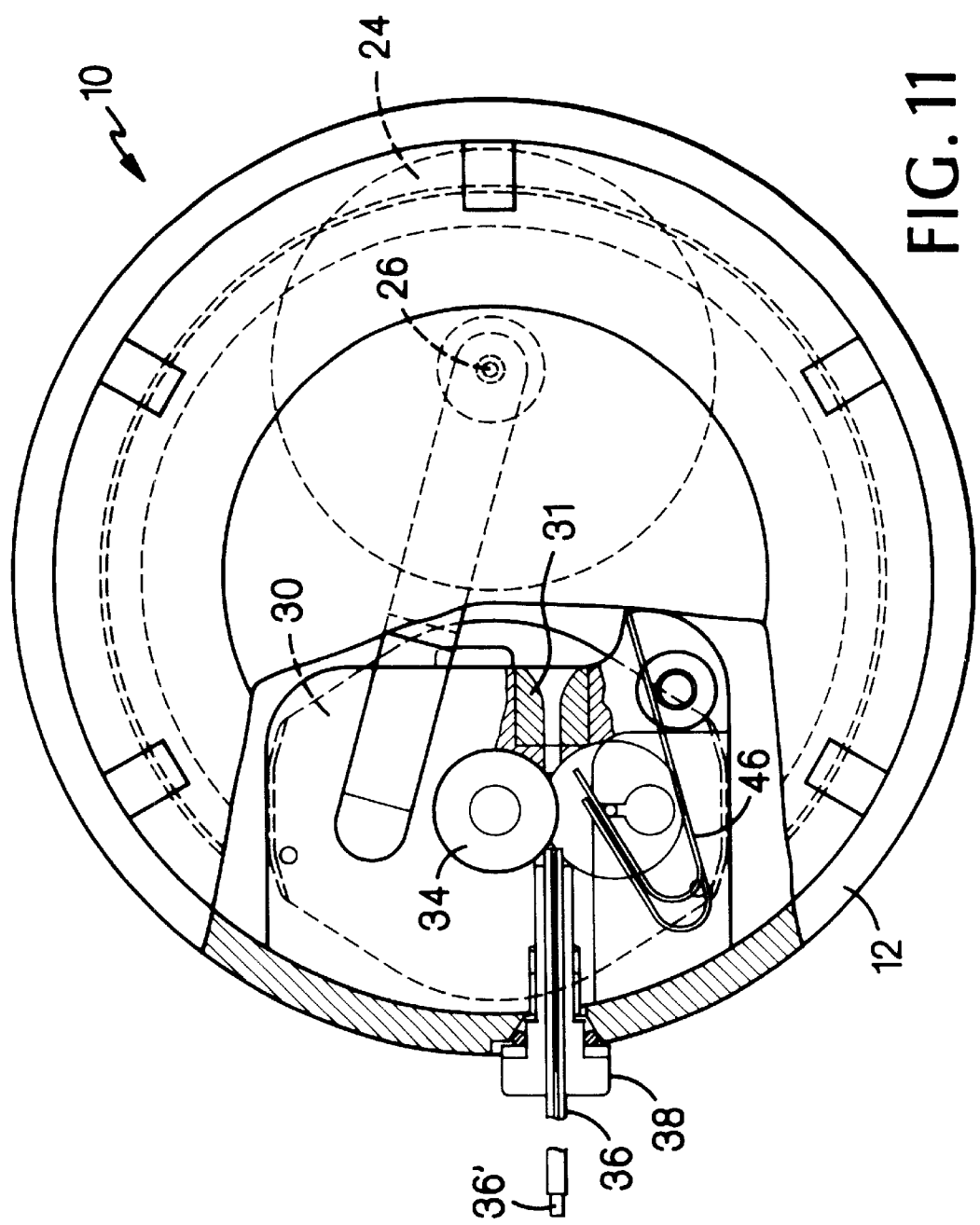
FIG. 11 is a top view in partial cross-section of the device of FIG. 10.

FIGS. 10 and 11 show a cylindrical implantable device designed in much the same way and with essentially the same components as the elongated device of FIGS. 6 to 9. Three devices were made following this design. Each device was made with a stainless steel or transparent POLYSULFONE™ housing 12 having an external diameter of about 3 cm and a height of 1.43 cm, and containing a bobbin 24 having a diameter of about 1.8 cm. Watch movement F. E. 6230 and watch battery PENATA 377 (Spain) were used in these devices. The motor wheel has a diameter of 4.4 mm, and the motor runs at 1 Hz, delivering about 1.1 mm of filament per hour.

The housing was filled with Dow Corning silicon oil 344 to prevent entry of water into the device. In addition, exit tube 36 was made of flexible TYGON™, and was filled with petroleum jelly to ensure that the filament can pass out of the device without allowing water to enter. As a further measure, a hollow stainless steel tube 36' (outer diameter of 0.5 mm) was press-fit into the flexible exit tube 36 (inner diameter 0.40 mm) to form a more precise exit port through which the filament passes.

Three of these devices were loaded with 25 cm long filaments of HPMC or nylon and implanted intraperitoneally into rats in separate tests. In the first test, the device was removed after 168 hours of operation and had delivered 18 cm of nylon filament. In the second test, the device was removed after 144 hours of operation and had delivered 16.5 cm of nylon filament. In the third test, the device was removed after 120.5 hours of operation and had delivered 13.5 cm of HPMC filament. In each of the three tests, there were no problems associated with the surgical implantation, the housing remained watertight, the mechanism remained operational, and the device was not affected by implantation.

These devices can deliver a wide variety of dosages depending on the nature of the solid filament, and the delivery rate. For example, a filament containing 50% drug, e.g., SOMATULINE™, and 50% carrier, e.g., HEC, with an external diameter of 0.28 mm, contains an average of 0.25 mg/cm of the drug. Thus, at a delivery rate of 1.2 mm/hr, a device containing this filament can deliver 0.03 mg/hr, or 0.7193 mg/day. At a rate of 0.4 mm/hr, this dosage can be precisely lowered to 0.01 mg/hr, or 0.2398 mg/day.

Other Implantable Devices

Figure 12:
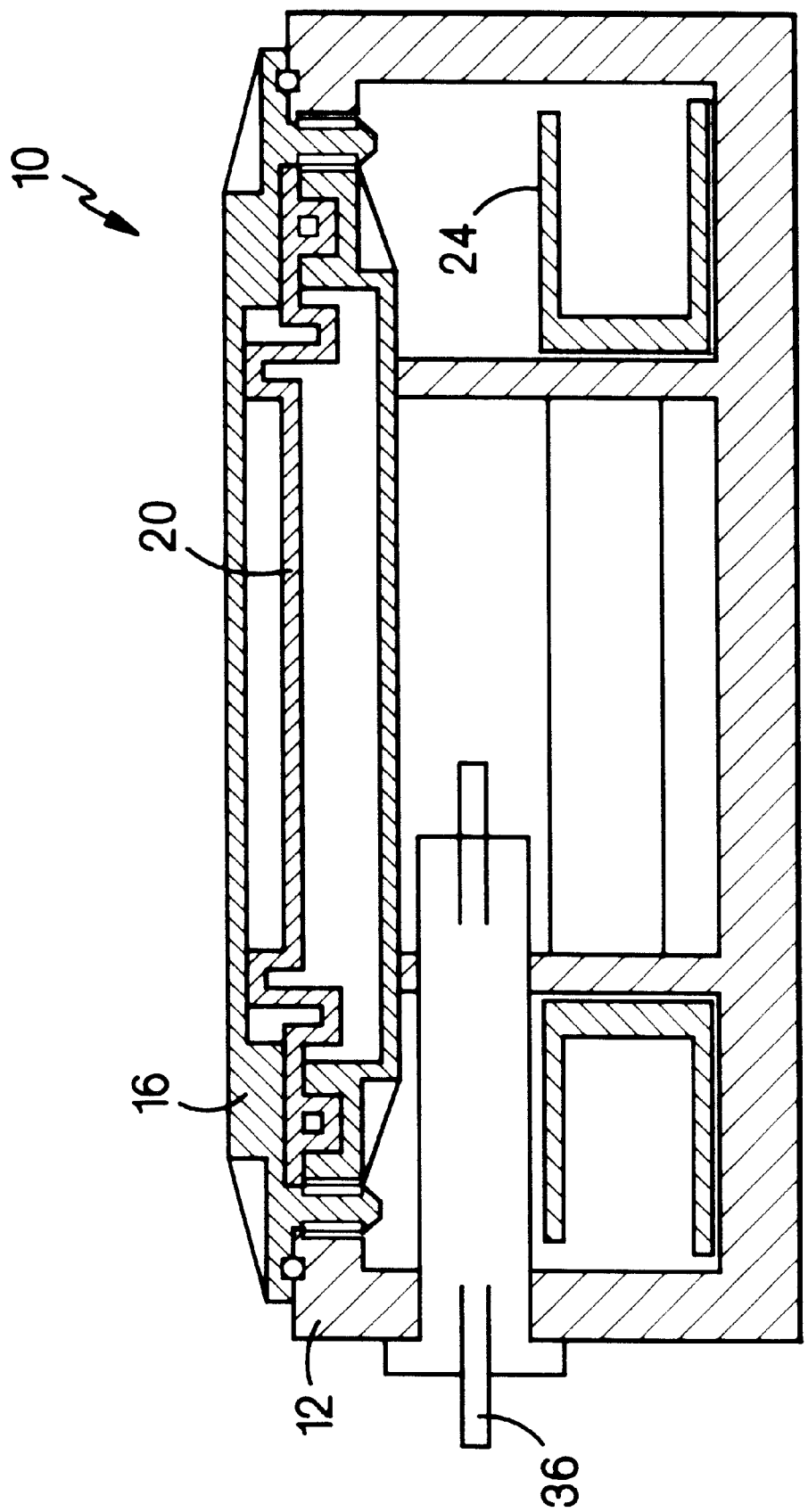
FIG. 12 is a side cross-sectional view of another cylindrical implantable solid drug composition filament delivery device in which the drug reservoir is a hollow bobbin.

FIG. 12 shows a schematic in cross-section of a cylindrical implantable device in which the bobbin is hollow and the motor and electronics are in the center of the bobbin. This allows a more physiological shape, and a constant angle of the filament on the bobbin by fixing a point on the housing for the transit area and unwinding the filament between the housing and the top of the bobbin.

In an alternative embodiment, the transit assembly can be designed to merely expose the filament or tape to the bodily fluids, and then to return the composition, now without any drug, to the device for collection on a take-up bobbin or spool. Such a device is preferably used in situations in which the carrier material is not to be left in the patient. For example, the transit area can be designed as a compartment or external surface of the housing which is open to the body fluids. Preferably, the compartment or surface comprises two openings, one to permit the filament or tape to exit the housing into the bodily fluids, and the second to permit the filament, now without a drug, to return into the,housing. The two openings allow the filament to pass without allowing bodily fluids to enter the device. For example, the openings may be sealed with O-rings.

Figure 14:
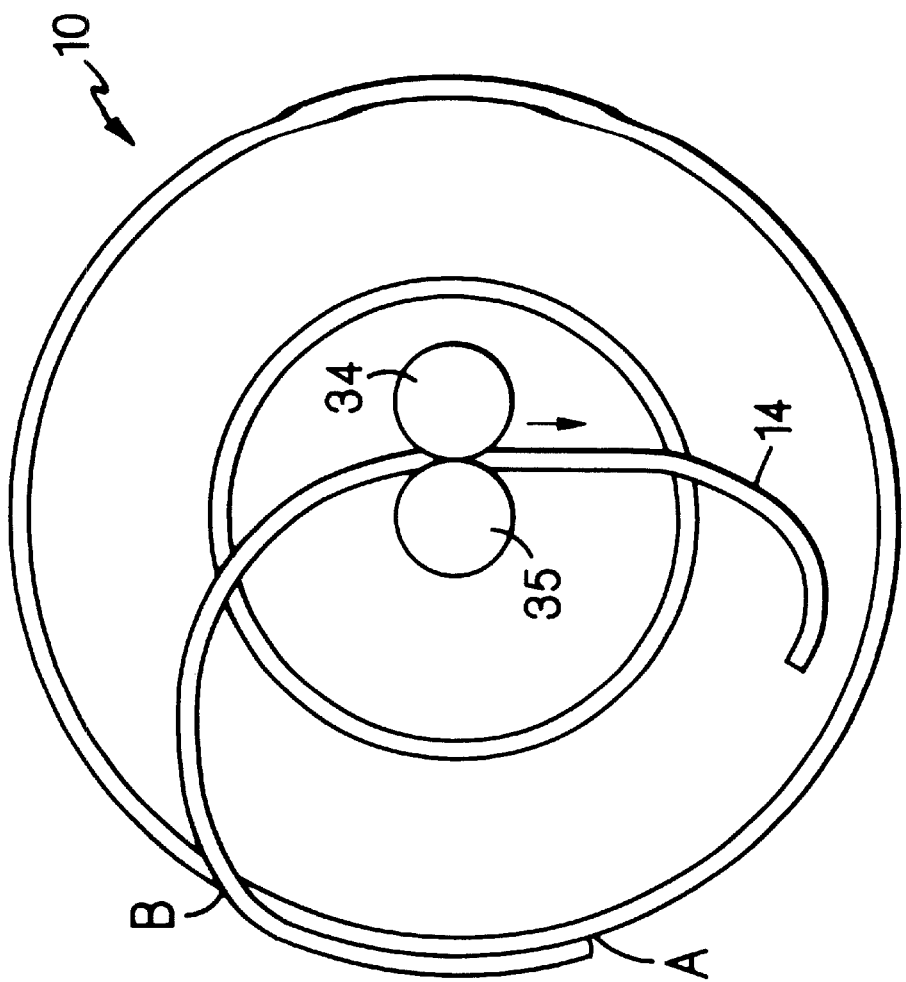
FIG. 14 is a schematic top view of the device of FIG. 13.
Figure 13:
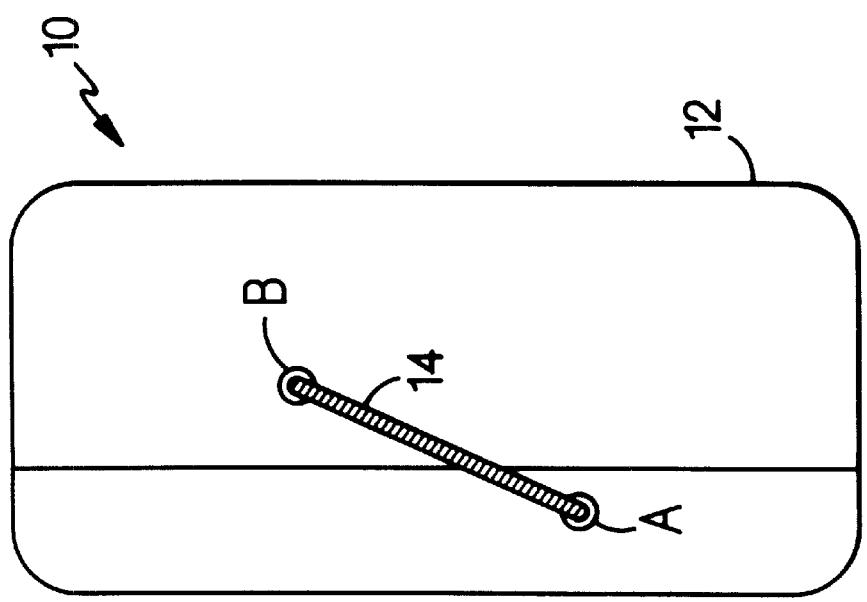
FIG. 13 is a schematic side plan view of a cylindrical implantable delivery device in which the filament is exposed to the bodily fluids and then recovered into the device.

FIGS. 13 and 14 show side and top (in partial section) schematic views of such a device that moves the filament 14 from a first reservoir, e.g., a dispensing bobbin 24, out of the device 10 through a first opening A in the housing 12, along the surface of the housing, and then pulls the filament by means of wheels 34 and 35 through a second opening B back into the housing for collection in a second reservoir, e.g., a space within the housing (as shown in FIG. 14) or on a pick-up bobbin.

In another embodiment, the transit area comprises an opening which is smaller than the drug composition, which for this embodiment is preferably in the form of a flat tape rather than a cylindrical filament, and the composition merely passes by the opening to expose the composition to the external environment, and is then collected on a take-up bobbin.

In another embodiment, the device is designed to be permanently implanted into a patient and be easily accessible, e.g., implanted near the skin to facilitate the reloading of the bobbin with a needle. In this embodiment, a loaded reservoir and a pre-programmed control mechanism can be designed as part of a cartridge that can be easily inserted into a receiving chamber in the housing through a small opening in the skin. Thus, the housing, motor, battery, and actuator mechanism all remain implanted within the patient, and only the drug reservoir and the optionally pre-programmed control mechanism are exchanged as required throughout extended therapy regimens. In an alternative embodiment, the battery is also included in the exchangeable cartridge.

Pen-Like Filament Injector Device

The solid drug compositions can also be dispensed in separate, single-dose injections from a small, light-weight pen-like filament injector that holds several days or weeks worth of drug dosages. When using this device, the patient is required to change only a needle before each injection, and there is no waste or need to refrigerate the solid drug composition. Rather, patients can carry the device with them, only having to refill the device after several days or weeks. These size and storage factors provide substantial improvements over existing pen injectors for liquid drug formulations. In addition, the relatively low cost of the devices allows them to be made disposable.

Figure 15:
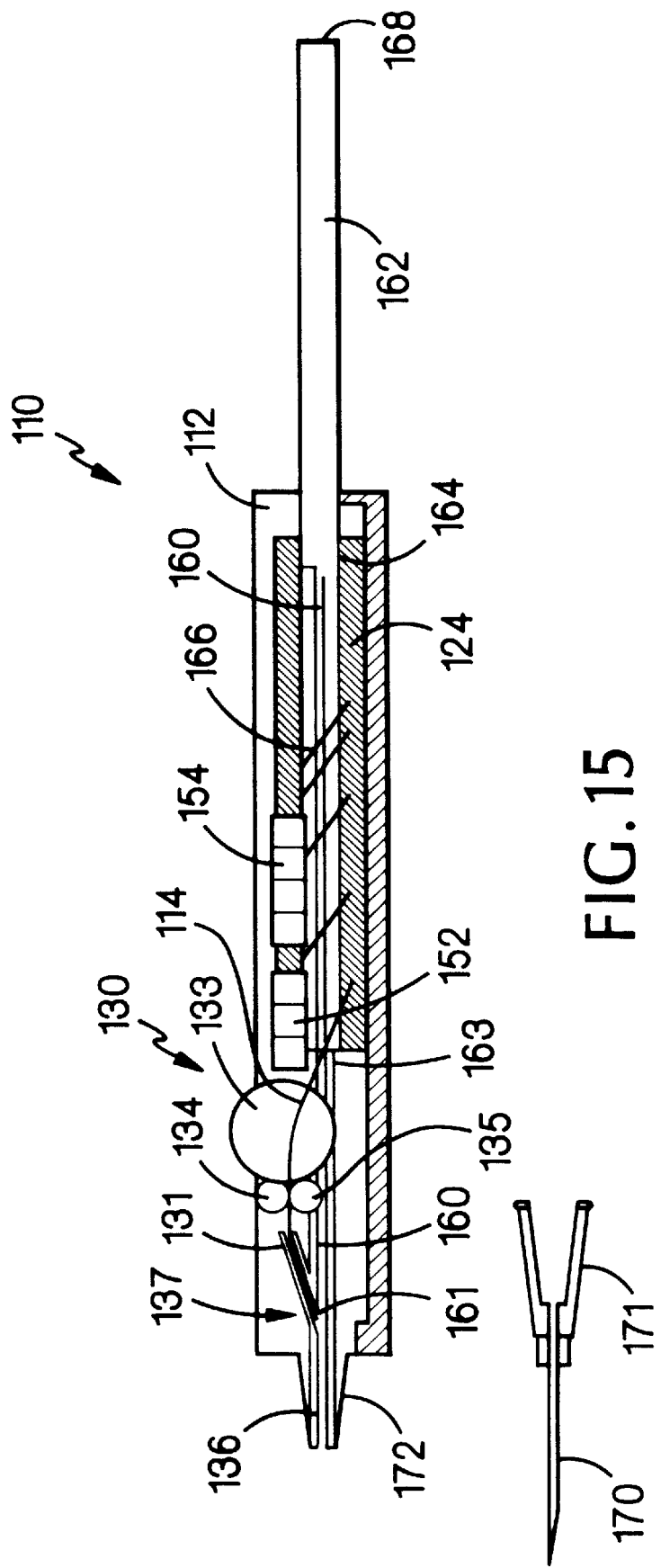
FIG. 15 is a cross-sectional view of a pen-like filament injecting device.
Figure 16:
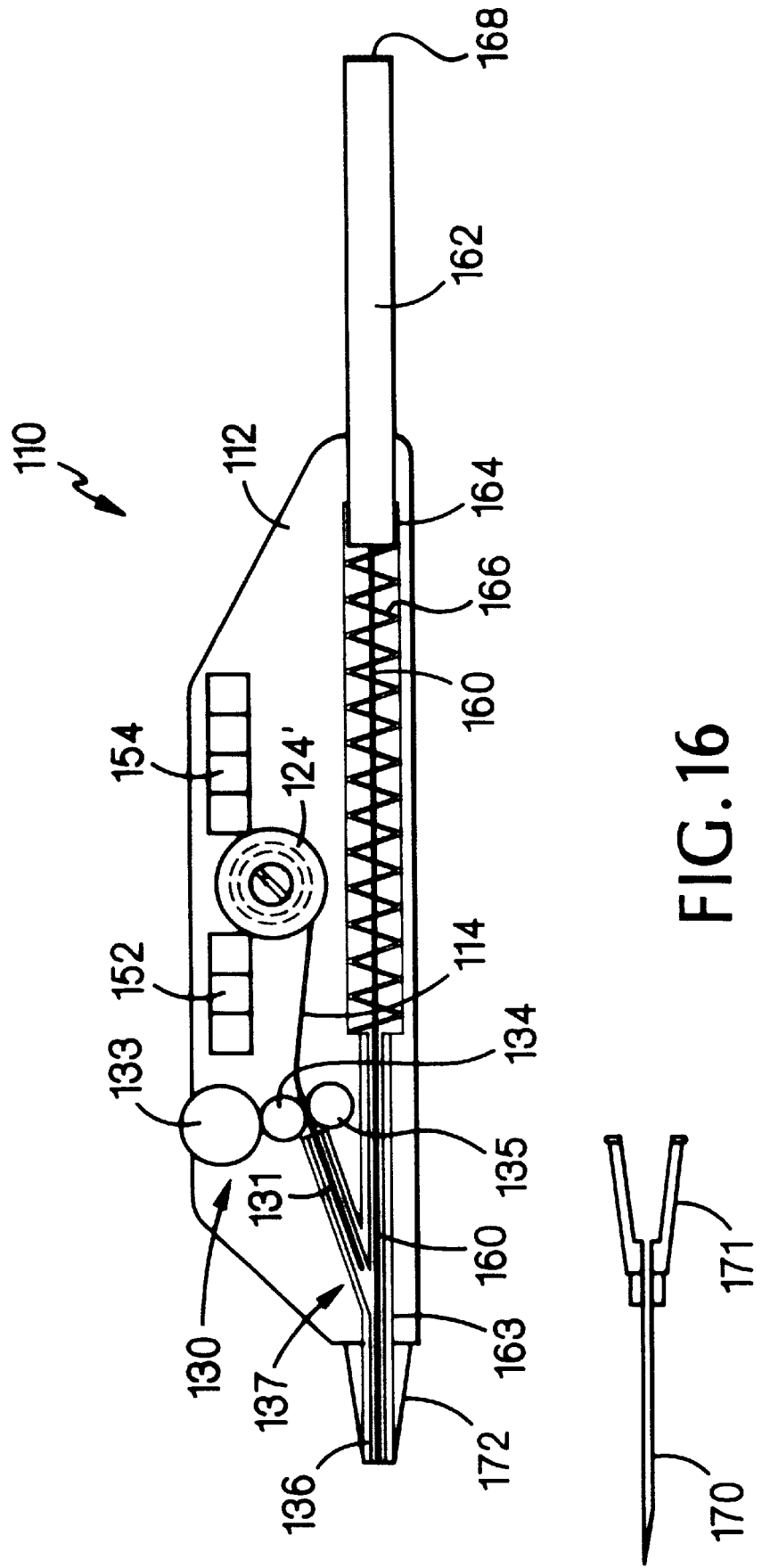
FIG. 16 is a cross-sectional view of another pen-like filament injecting device.

FIGS. 15 and 16 show two embodiments of such pen-like injection devices. Pen-like device 110 includes a barrel-shaped housing 112, which can be machined or molded from a suitable heat resistant, rigid material, e.g., polyvinyl chloride, polycarbonate, TEFLON®, POLYSULFONE® (Amoco), or stainless steel. The housing may be transparent to facilitate the determination of whether filament 114 is properly moving though the device. The external dimensions of the housing can be about 10 cm in length and 1 cm in diameter.

The housing encloses a reservoir for the solid drug composition filament. This reservoir can be, e.g., an open compartment 124 (FIG. 15) or a removable bobbin 124' (FIG. 16). Typically, filament 114 is wrapped around the bobbin before the bobbin is inserted into the housing. In other embodiments, the bobbin is permanently installed in the housing and is loaded with drug filament. Filament 114 is initially fed from the reservoir into an actuator 130, which includes wheels 134 and 135, and a manipulator wheel 133. Manipulator wheel 133 allows the user to rotate the wheels which contact and pull the filament from the reservoir and into feed tube 131 which leads to a transit area 137 in which the filament is cut and dispensed out delivery tube 136.

Actuator 130 supports the wheels 134 and 135 and the manipulator wheel 133. The wheels can be gear wheels or smooth-surfaced wheels or rollers, e.g., of rubber or plastic, as long as they can contact and move the solid drug composition from the reservoir through the actuator and into the transit area. These wheels are attached to the actuator by gear pins and rotation of the wheels can be enhanced by washers, both in a conventional manner. The wheels rotate in opposite directions such that filament 114 is moved between them and towards feed tube 131. Preferably, the spacing between the two wheels is slightly less than the diameter of filament 114.

The wheels are rotated by manipulator wheel 133, which engages wheel 134. The manual rotation of manipulator wheel 133 causes wheel 134 to rotate, which in turn causes wheel 135 to rotate in the opposite direction, thereby causing the filament to move between wheels 134 and 135. The manipulator wheel is preferably manufactured from rubber or plastic with gear teeth which engage gear teeth located on wheel 134. The manipulator wheel protrudes through housing 112 to allow physical manipulation by the user. The user rotates the manipulator wheel such that the wheels rotate, thereby transporting a specific length of filament to feed tube 131 where it is subsequently cut and injected by microplunger 160.

In another embodiment, manipulator wheel 133 is replaced with a push button that engages the two drive wheels causing them to rotate a specific amount.

Device 110 also preferably includes a delivery counter 152, which is connected to actuator 130. The delivery counter measures the rotation of manipulator wheel 133. Preferably, the counter displays the amount of drug (e.g., in IU or mg) delivered to feed tube 131. A security control counter 154 is also attached to the actuator. This control displays the amount of drug present in the device at the beginning of each use. As manipulator wheel 133 is rotated, the counter records this information, thus indicating the remaining supply of drug in the reservoir. The security counter can also be designed to limit the maximum delivery of drug in each injection.

The plunger mechanism for this device includes an external plunger 162, microplunger 160, guide tube 163, plunger holder 164, and repositioner 166. External plunger 162 is preferably manufactured from a suitable rigid material, e.g., plastic or stainless steel, and is free to move through housing 112 within plunger holder 164. Preferably, external plunger 162 includes a knob (not shown) which interacts with plunger holder 164 to prevent the plunger from completely exiting the housing. External plunger 162 includes thumb-rest 168 to easily press the plunger into the housing 112.

Microplunger 160 is attached to external plunger 162, and is preferably manufactured from a suitable rigid material, e.g., stainless steel or plastic. Microplunger 160 moves freely through guide tube 163 and delivery tube 136. The guide and delivery tubes can be formed from a single tube, or from two separate tubes of equal internal diameter. The external diameter of the microplunger is preferably slightly less than the diameter of delivery and guide tubes, e.g., about 0.5 mm, and preferably 0.2 to 0.35 mm.

External plunger 160 protrudes from housing 112 approximately the combined length of delivery tube 136 and needle 170. Thus, when external plunger 162 is pressed into the housing, microplunger 160 moves into and through delivery tube 136 and needle 170, and injects a precise length of filament 114 (114' in FIG. 17B) into the patient as described in greater detail below.

Preferably, the plunger system includes a repositioner 166, e.g., in the form of a spring. In one embodiment, repositioner 166 is preferably made of a rigid, yet flexible substance, e.g., stainless steel. The spring should be able to be compressed when external force is applied to the external plunger 162, and then re-expand when the force is removed. In another embodiment, to ensure complete delivery of drug filament 114, repositioner 166 is activated only when microplunger 160 has reached the tip of needle 170.

Figure 17:
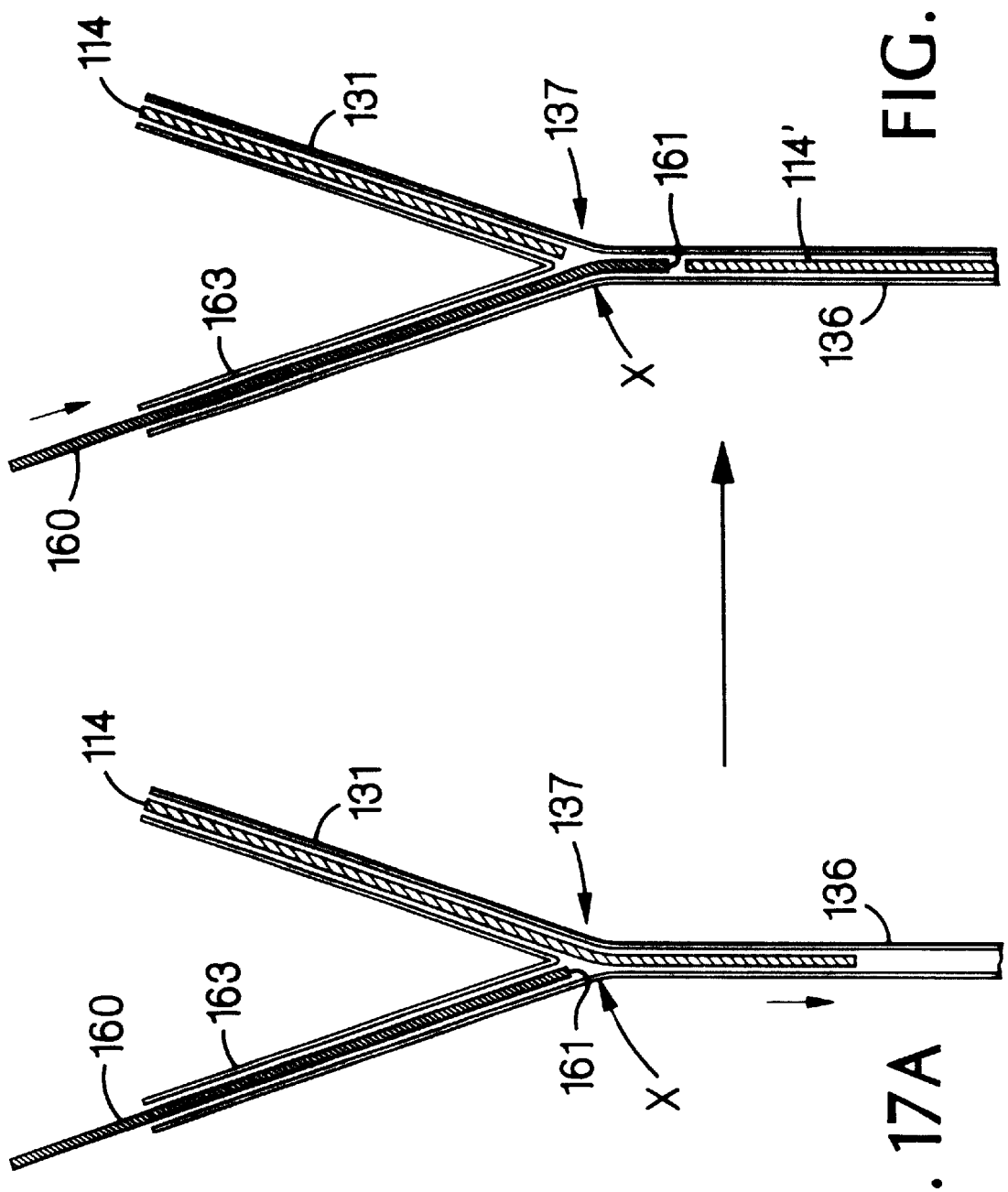
FIGS. 17A and 17B are schematic cross-sectional views of the cutting and dispensing mechanism of the filament injecting device of FIG. 15.

The transit area 137 includes a feed tube 131, a delivery tube 136, a cutting mechanism 161 on the end of microplunger 160 opposite plunger 162, and tip 172, which encloses a portion of the delivery tube. With reference to FIGS. 17A and 17B, feed tube 131 and guide tube 163 form the two arms of a "Y" and delivery tube 136 forms the base of the "Y". All of these tubes are preferably manufactured from suitable rigid material, e.g., stainless steel. By manually engaging manipulator wheel 133, the solid drug composition filament 114 is moved from actuator 130 into feed tube 131 and then into delivery tube 136. By depressing external plunger 162, cutting mechanism 161 of microplunger 160 moves from guide tube 163 to position X in FIG. 17A. The cutting mechanism contacts filament 114 at position X, and subsequently cuts the filament at this position. Microplunger 160 then proceeds to force the cut portion of the filament 114' through delivery tube 136 and into needle 170.

Figure 18:
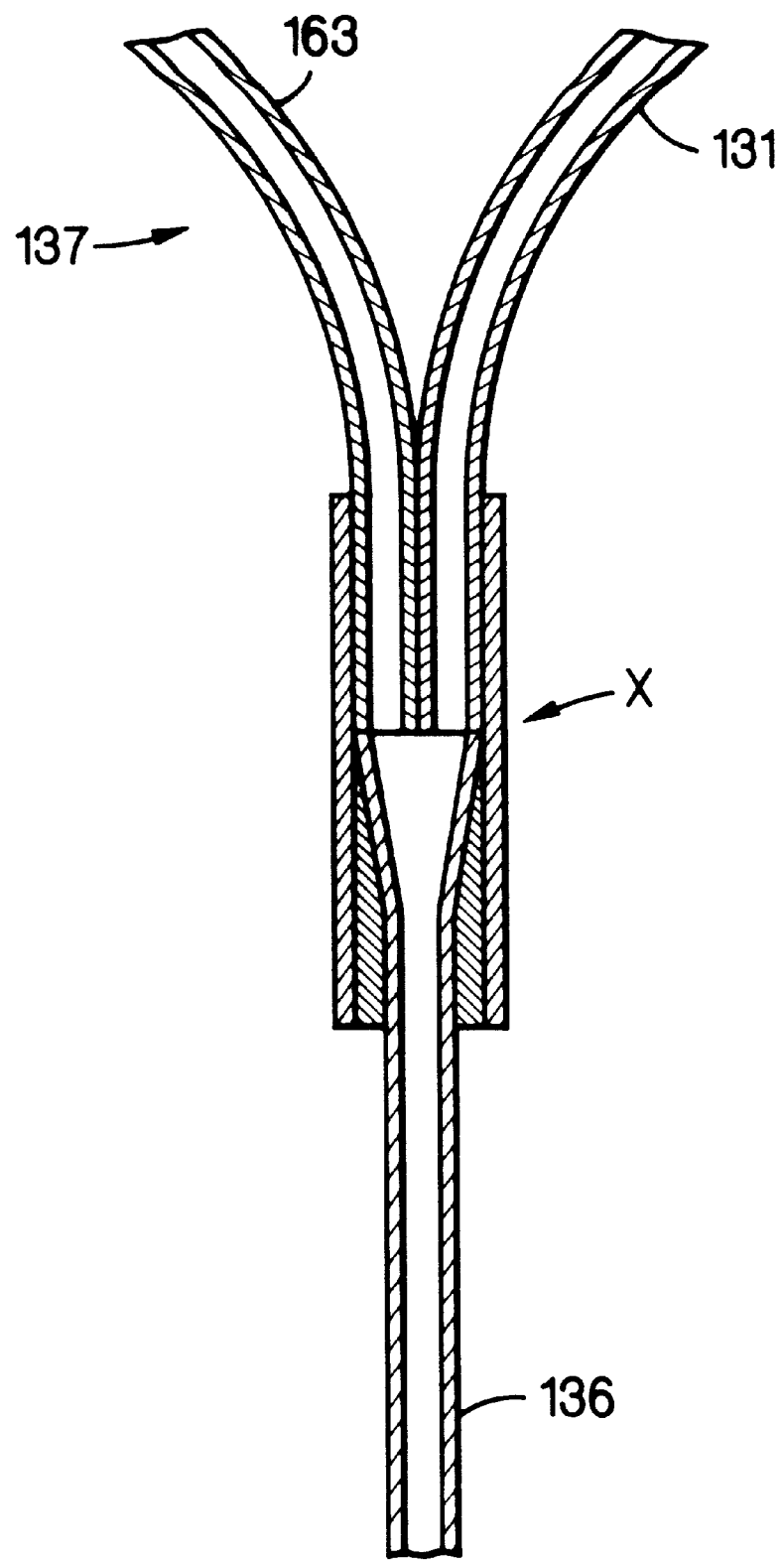
FIG. 18 is a schematic cross-section of an alternative cutting mechanism and transit area of the filament injecting device of FIG. 15.

FIG. 18 shows an alternative embodiment of transit area 137, in which delivery tube 136 has a funnel-shaped opening at position X, and feed tube 131 and guide tube 163 are curved.

Transit area 137 also includes tip 172 that encompasses the part of delivery tube 136 which is outside housing 112. This tip may be machined or molded as part of the housing, and is preferably conical in shape to allow easy attachment to standard needles, e.g., shaped like the conical end of a standard syringe.

Needle 170 is preferably a standard needle which includes a connector 171. Preferably, the internal shape of connector 171 is slightly smaller than the external shape of tip 172 such that needle 170 can be attached to tip 172 by frictional force. In other embodiments, connector 171 includes a locking mechanism allowing the firm connection of the needle to tip 172, e.g., a standard luer-lock mechanism.

When attached, the receiving end of needle 170 should be directly in line with delivery tube 136. The inner diameter of needle 170 is preferably the same as the inner diameter of delivery tube 136, allowing filament portion 114' easy transit from tube 136, through needle 170, and out into the patient.

In other embodiments, tip 172 comprises a security mechanism that locks actuator 130 when needle 170 is not attached to the tip. Preferably, the security mechanism makes it impossible to either rotate manipulator wheel 133 or depress plunger 162 before the needle is attached. After the connection of needle 170, the manipulator wheel 133 can be rotated and external plunger 162 is reactivated. Once external plunger 162 has been depressed, manipulator wheel 133 cannot be rotated until a new needle 170 has been attached to tip 172.

FIG. 16 shows another embodiment of the pen-like injector device, in which the filament is stored on a bobbin 124', rather than loosely in a reservoir compartment. Otherwise, the separate parts and their functions are essentially the same as in the embodiment of FIG. 15, and are given the same reference numerals.

EXAMPLE

A 0.3 mm diameter filament was fed into a pen injector having a guide and delivery tube of 0.38 mm internal diameter. The device was tested with two different plungers, one with an external diameter of 0.3 mm, and the second with a 0.35 external diameter. The device was set to cut the filament into lengths of precisely 12.0 mm. The table below shows the results of these experiments.

TABLE

| N° | 0.30 mm Plunger | | 0.35 mm Plunger | |
| --- | --- | --- | --- | --- |
| | Length (mm) | Weight (mg) | Length (mm) | Weight (mg) |
| 1 | 11.50 | 0.2497 | 12.00 | 0.2825 |
| 2 | 12.00 | 0.2580 | 12.00 | 0.2743 |
| 3 | 11.50 | 0.2550 | 12.00 | 0.2728 |
| 4 | 12.00 | 0.2693 | 12.00 | 0.2747 |
| 5 | 12.00 | 0.2629 | 12.00 | 0.2701 |
| 6 | 12.00 | 0.2604 | 12.50 | 0.2798 |
| Mean | 11.83 | 0.2592 | 12.08 | 0.2757 |
| SD | 0.25 | 0.0067 | 0.2041 | 0.0046 |
| RSD | 2.18% | 2.59% | 1.69% | 1.67% |

As shown in the Table, the 0.35 mm plunger delivered accurate dosage, and provides the necessary precision to dispense 12.0±0.5 mm long segments of filament that provide 0.2757±0.0068 mg of, e.g., SOMATULINE™ in a composition of 50% SOMATULINE™ acetate, and 50% HEC, as described above.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications within the scope of the invention will be apparent to those skilled in the art to which the invention pertains.

For example, the micro-mechanical delivery devices can be used to deliver active ingredients other than drugs, and can be used to deliver precise quantities of active ingredients, e.g., fertilizers, air fresheners, or nutrients for plants or animals, in any environment, e.g., in air or in a liquid environment, according to an adjustable delivery profile as described above.

What is claimed is:

1. A method of automatically administering a drug to a patient according to a predetermined delivery profile, the method comprising:
   obtaining a device comprising
      a housing;
      a reservoir operatively connected to the housing and loaded with a solid composition comprising the drug;
      a transit assembly attached to said housing and configured to allow the solid composition to pass out of the housing;
      an actuator arranged within the housing to move the solid composition from the reservoir to a transit assembly, wherein the solid composition exits the housing at the transit assembly, and
      a controller that acts on the actuator to adjust movement of the solid composition out of the housing according to the predetermined delivery profile;
   programming the controller of the device to cause the actuator to move the solid composition to the transit area according to the predetermined delivery profile;
   bringing the transit area into contact with the body fluids of the patient, and
   providing energy to the controller and the actuator to move the composition from the reservoir to the transit area to deliver the drug to body fluids of the patient according to the predetermined delivery profile.

2. A method of claim 1, wherein said delivery profile changes over time.

3. A method of claim 1, wherein said transit area is brought into contact with the body fluids of the patient by implanting said device into the patient.

4. A method of claim 1, wherein said drug is administered to the patient continuously for over 3 months according to said delivery profile.

5. A method of making a solid drug filament, said method comprising;

preparing a non-solid form of said drug, extruding said non-solid drug into an elongate filament having a cross-section of less than 0.5 mm and a surface area to drug ratio of at least 10 square millimeters per milligram of said drug, and solidifying said filament to form the solid drug filament.

6. A method of claim 5, wherein said non-solid form of said drug is prepared by mixing a carrier with a sufficient amount of a solvent to form a gel and mixing said gel with said drug to form a homogeneous, non-solid form, and further wherein said filament is solidified by removing said solvent.

7. A method of claim 5, wherein said non-solid form of said drug is prepared by mixing a carrier with said drug to form a mixture and heating said mixture to a temperature above a melting point of said carrier to generate said non-solid form, and further wherein said filament is solidified by cooling to a temperature below said melting point of said carrier.

* * * * *